US011607389B2

(12) United States Patent
Sherman et al.

(10) Patent No.: US 11,607,389 B2
(45) Date of Patent: *Mar. 21, 2023

(54) DELAYED RELEASE DEFERIPRONE TABLETS AND METHODS OF USING THE SAME

(71) Applicant: Chiesi Farmaceutici S.p.A., Parma (IT)

(72) Inventors: Bernard Charles Sherman, Toronto (CA); Michael Spino, Pickering (CA)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/742,960

(22) Filed: May 12, 2022

(65) Prior Publication Data

US 2022/0265559 A1    Aug. 25, 2022

Related U.S. Application Data

(63) Continuation of application No. 17/327,135, filed on May 21, 2021, which is a continuation of application No. 16/714,520, filed on Dec. 13, 2019, which is a continuation of application No. 16/171,170, filed on Oct. 25, 2018, now Pat. No. 10,940,116.

(60) Provisional application No. 62/596,043, filed on Dec. 7, 2017, provisional application No. 62/577,055, filed on Oct. 25, 2017.

(51) Int. Cl.

| A61K 9/28 | (2006.01) |
|---|---|
| A61K 9/20 | (2006.01) |
| A61K 31/4412 | (2006.01) |
| A61K 31/4422 | (2006.01) |
| A61P 7/06 | (2006.01) |
| A61P 25/28 | (2006.01) |
| A61P 35/00 | (2006.01) |

(52) U.S. Cl.
CPC ............ *A61K 9/2833* (2013.01); *A61K 9/204* (2013.01); *A61K 9/2009* (2013.01); *A61K 9/2018* (2013.01); *A61K 9/2027* (2013.01); *A61K 9/2054* (2013.01); *A61K 9/2072* (2013.01); *A61K 9/284* (2013.01); *A61K 31/4412* (2013.01); *A61K 31/4422* (2013.01); *A61P 7/06* (2018.01); *A61P 25/28* (2018.01); *A61P 35/00* (2018.01)

(58) Field of Classification Search
CPC .................................. A61P 7/06; A61K 9/2833
See application file for complete search history.

(56) References Cited

U.S. PATENT DOCUMENTS

| 7,049,328 | B2 | 5/2006 | Spino et al. |
|---|---|---|---|
| 8,263,125 | B2 | 9/2012 | Vaya et al. |
| 8,268,352 | B2 | 9/2012 | Vaya et al. |
| 8,563,035 | B2 | 10/2013 | Cifter et al. |
| 8,703,156 | B2 | 4/2014 | Spino et al. |
| 10,780,055 | B2 | 9/2020 | Sherman et al. |
| 10,940,115 | B2 | 3/2021 | Sherman et al. |
| 10,940,116 | B2 | 3/2021 | Sherman et al. |
| 11,357,731 | B2* | 6/2022 | Sherman .................. A61P 7/06 |
| 2008/0085306 | A1 | 4/2008 | Nangia et al. |
| 2009/0023784 | A1 | 1/2009 | Munnich et al. |
| 2010/0255082 | A1 | 10/2010 | Chauhan et al. |
| 2011/0039911 | A1 | 2/2011 | Pe'Ery |
| 2012/0053212 | A1 | 3/2012 | Shag |
| 2012/0189692 | A1 | 7/2012 | Cullen et al. |
| 2013/0023569 | A1 | 1/2013 | Spino et al. |
| 2014/0314676 | A1 | 10/2014 | Spino et al. |
| 2014/0364491 | A1 | 12/2014 | Bortz |
| 2018/0036228 | A1 | 2/2018 | Burke et al. |
| 2019/0117581 | A1 | 4/2019 | Sherman et al. |
| 2019/0125682 | A1 | 5/2019 | Sherman et al. |
| 2020/0188309 | A1 | 6/2020 | Sherman et al. |
| 2020/0237674 | A1 | 7/2020 | Sherman et al. |
| 2020/0253945 | A1 | 8/2020 | Sherman et al. |
| 2020/0268672 | A1 | 8/2020 | Sherman et al. |
| 2021/0386677 | A1 | 12/2021 | Sherman et al. |

FOREIGN PATENT DOCUMENTS

| CA | 2505476 A1 | 5/2004 |
|---|---|---|
| CA | 2819234 A1 | 7/2012 |
| CN | 101352438 A | 1/2009 |
| IN | 247315 | 4/1999 |
| IR | 90-07-27-71996 | 12/2011 |
| WO | WO-9718805 A1 | 5/1997 |
| WO | WO-9825905 A1 | 6/1998 |

(Continued)

OTHER PUBLICATIONS

Agrawal, S., et al., "Mitochondrial iron dysregulation in mouse and human Huntington's disease brain, Presented at Society for Neuroscience," Nov. 11-15, 2017, Washington D.C., United States, 1 page.

Agrawal, M.B, et al., "Deferiprone (KELFER), how to Make it Work More Widely, Effectively and Without Adverse Effects: An Indian Study." 1 page, 9th International Conference on Oral Chelation, Hamburg, Germany (1999).

Aguilar-De-Leyva, A., et al., "A New Deferiprone Controlled Release System Obtained by Ultrasound-assisted Compression," *Pharmaceutical Development and Technology* 19(6):728-734, Informa Healthcare, United Kingdom (Sep. 2014).

(Continued)

*Primary Examiner* — Gina C Justice
(74) *Attorney, Agent, or Firm* — Sterne, Kessler, Goldstein & Fox P.L.L.C.

(57) ABSTRACT

The invention is directed to pharmaceutical compositions such as tablets that exhibit delayed release properties when administered as either whole or half tablets. The invention is also directed to delayed release tablets comprising deferiprone for oral administration, for which twice daily administration is bioequivalent to the same daily dose of an immediate release tablet administered thrice daily. The invention is also directed to methods of making and using the same.

24 Claims, 4 Drawing Sheets

(56) References Cited

FOREIGN PATENT DOCUMENTS

| | | |
|---|---|---|
| WO | WO-0149266 A2 | 7/2001 |
| WO | WO-0202114 A1 | 1/2002 |
| WO | WO-2004006856 A2 | 1/2004 |
| WO | WO-2006017650 A2 | 2/2006 |
| WO | WO-2008066862 A2 | 6/2008 |
| WO | WO-2009155088 A1 | 12/2009 |
| WO | WO-2010005851 A1 | 1/2010 |
| WO | WO-2010069920 A1 | 6/2010 |
| WO | WO-2011032000 A2 | 3/2011 |
| WO | WO-2013075015 A1 | 5/2013 |
| WO | WO-2013139931 A1 | 9/2013 |
| WO | WO-2014072673 A1 | 5/2014 |
| WO | WO-2015087258 A1 | 6/2015 |

OTHER PUBLICATIONS

Al-Refaie, F.N., et al., "Oral Iron-chelating Therapy: the L1 Experience," *Baillière's Clinical Haematology* 7(4):941-963, Bailliere Tindall, United Kingdom (Dec. 1994).

Anderson, L.J., et al., "Comparison of Effects of Oral Deferiprone and Subcutaneous Desferrioxamine on Myocardial Iron Concentrations and Ventricular Function in Beta-thalassaemia," *Lancet* 360: 516-520, Elsevier, United Kingdom (Aug. 2002).

Azarkeivan, A., et al., "Evaluation of gastric side effects of new form of Deferiprone, (L1; Enteric coated) in Thalassemia major patients," *Sci J Iran Blood Transfus Organ* 13(3): 163-169, Iranian Blood Transfusion Organization Research Center, Iran (2016).

Cabantchik, Z.I., et al., "Regional siderosis: a new challenge for iron chelation therapy," *Frontiers in Pharmacology* 4(167): 1-7, Frontiers, Switzerland (2013).

Chen, J., et al., "Iron Accumulates in Huntington's Disease Neurons: Protection by Deferoxamine," *PLOSlone* 8(10):e77023, pp. 1-12, Public Library of Science, United States (2013).

Clinical Trials. Retrieved from the Internet: (URL: https://clinicaltrials.gov/ct2/results?term=deferiprone&no_unk=Y). (retrieved on Nov. 15, 2018).

Cossu, G., et al., "Efficacy and safety of deferiprone for the treatment of pantothenate kinase-associated neurodegeneration (PKAN) and neurodegeneration with brain iron accumulation (NBIA): results from a four years follow-up," *Parkinsonism & Related Disorders* 20(6):651-654, Elsevier, Netherlands (2014).

Crosland, R.D., et al., "Action of Reactive Oxygen Species and Their Antagonists on Twitch Tension of the Rat Phrenic Nerve-diaphragm," *Pharmacology & Toxicology* 77(3):231-237, Nordic Pharmacological Society: Distributed by Blackwell Munksgaard, Denmark (Sep. 1995).

Eleftheriou A., "About Thalassemia," Thalassemia International Federation, pp. 1-178 (2003).

Galanello, R., "Deferiprone in the treatment of transfusion-dependent thalassemia: a review and perspective," *Ther Clin Risk Manag.* 3(5):795-805, Dovepress, United Kingdom (2007).

Grady, R.W and Giardina, P.J., "Iron Chelation: Rationale for Combination Therapy," *Iron Chelators: New Development Strategies*, pp. 293-310 Ponte Vedra Beach, FL: Saratoga group (2000).

Grady, R.W., et al., "Iron Chelation: Combined Therapy May Be a Better Approach." 1 page, 9th International Conference on Oral Chelation, Hamburg, Germany (1999).

Grubman, A., et al., "Mitochondrial Metals as a Potential Therapeutic Target in Neurodegeneration," *British Journal of Pharmacology* 171(8): 2159-2173, Wiley, United Kingdom (Apr. 2014).

Hatcher, H.C., et al., "Synthetic and Natural Iron Chelators: Therapeutic Potential and Clinical Use," *Future Medicinal Chemistry* 1(9), pp. 1-35 Future Science, United Kingdom (Dec. 2009).

Heli, H., et al., "Advances in Iron Chelation: an Update," *Expert Opinion on Therapeutic Patents* 21(6): 819-856, Informa Healthcare, United Kingdom (Jun. 2011).

Hoffbrand, A.V, "Oral Iron Chelation," *Seminars in Hematology* 33(1): 1-8, W.B. Saunders, United States (Jan. 1996).

Kakhlon, O., et al., "Iron Redistribution as a therapeutic strategy for treating diseases of localized iron accumulation," *Canadian Journal of Physiology and Pharmacology* 88(3):187-196, NRC Research Press, Canada (2010).

Kaul, D. and Taram, S.V., "Dual Control over release of a water soluble drug from compressed tablets," *Indian Journal of Pharmaceutical Sciences* 56(1);15-18, The Indian Pharmaceutical Society, India (1994).

Kaul, D. and Venkataram, S., "Sustained Release Tablet Formulation for a new Iron Chelator," *Drug Development and Industrial Pharmacy* 18(9):1023-1035, Taylor & Francis, United Kingdom (1992).

Kaul, D., et al., "Crystal Habit modifications and altered tableting characteristics," *International Journal of Pharmaceutics* 88(1-3):345-350, Elsevier, Netherlands (1992).

Kontoghiorghes, G.J., et al., "Safety Issues of Iron Chelation Therapy in Patients With Normal Range Iron Stores Including Thalassaemia, Neurodegenerative, Renal and Infectious Diseases," *Expert Opinion on Drug Safety* 9(2):201-216, Taylor & Francis, United Kingdom (Mar. 2010).

Kontoghiorghes, G.J., et al., "Benefits and Risks of Deferiprone in Iron Overload in Thalassaemia and Other Conditions: Comparison of Epidemiological and Therapeutic Aspects With Deferoxamine," *Drug Safety* 26(8):553-584, Springer International, New Zealand (2003).

Kontoghiorghes, G.J., et al., "Risk/benefit Assessment, Advantages Over Other Drugs and Targeting Methods in the Use of Deferiprone as a Pharmaceutical Antioxidant in Iron Loading and Non Iron Loading Conditions," *Hemoglobin* 33(5):386-397, Informa Healthcare, United Kingdom (2009).

Kontoghiorghes, G.J., et al., "The Role of Iron and Chelators on Infections in Iron Overload and Non Iron Loaded Conditions: Prospects for the Design of New Antimicrobial Therapies," *Hemoglobin* 34(3):227-239, Informa Healthcare, United Kingdom (Jun. 2010).

Kwiatkowski, A., et al., "Long-term Improvement Under Deferiprone in a Case of Neurodegeneration With Brain Iron Accumulation," *Parkinsonism and Related Disorders* 18(1):110-112, Elsevier Science, United Kingdom (Jan. 2012).

NCT02465489, Trial No. LA51-0115, "Single-dose pharmacokinetic study of deferiprone extended release tablets versus Ferriprox immediate release tablets under fasting and fed condition in healthy volunteers," ClinicalTrials.gov, Phase 1 (accessed at URL: https://clinicaltrials.gov/ct2/show/NCT02465489?term=LA51-0115&draw=1&rank=1) on Jul. 20, 2020.

Levy, M., et al., "Pilot safety trial of deferiprone in 10 subjects with superficial siderosis," *Stroke* 43(1): 120-124, Lippincott Williams & Wilkins, United States (2012).

Maggio, A., et al., "Deferiprone Versus Deferoxamine in Patients With Thalassemia Major: a Randomized Clinical Trial," *Blood Cells, Molecules and Diseases* 28(2):196-208, Academic Press, United States (Mar.-Apr. 2002).

Moreau, C., et al., "Could conservative iron chelation lead to neuroprotection amyotrophic lateral sclerosis?," *Antioxid Redox* 29(8), 17 pages Mary Ann Liebert, United States (2018).

Morel, I., et al., "Antioxidant and Free Radical Scavenging Activities of the Iron Chelators Pyoverdin and Hydroxypyrid-4-ones in Iron-loaded Hepatocyte Cultures: Comparison of Their Mechanism of Protection With That of Desferrioxamine," *Free Radical Biology and Medicine* 13(5):499-508, Elsevier Science, United States (Nov. 1992).

NCT02442310, Comparison of Deferiprone Delayed Release tablets and Deferiprone Oral Solution in Healthy Volunteers, ClinicalTrials.gov, published May 13, 2016 (accessed at https://clinicaltrials.gov/ct2/show/NCT02442310, accessed on May 25, 2017).

Peng, C-T., et al., "Safety Monitoring of Cardiac and Hepatic Systems in Beta-thalassemia Patients With Chelating Treatment in Taiwan," *European Journal of Haematology* 70(6):392-397, Blackwell, United Kingdom (Jun. 2003).

Pennell, D.J., et al., "Randomized Controlled Trial of Deferiprone or Deferoxamine in Beta-thalassemia Major Patients With Asymptomatic Myocardial Siderosis," *Blood* 107(9):3738-3744, American Society of Hematology, United States (May 2006).

(56) References Cited

OTHER PUBLICATIONS

Reeder, B.J., et al., "Tyrosine as a Redox-active Center in Electron Transfer to Ferryl Heme in Globins," *Free Radical Biology and Medicine* 44(3):274-283, Elsevier Science, United States (Feb. 2008).

Sheth, S., "Iron Chelation: an update." *Curr Opin Hematol* 21(0), pp. 1-7 Wolters Kluwer, Netherlands (2014).

Song, D., et al., "Systemic administration of the iron chelator deferiprone protects against light-induced photoreceptor degeneration in the mouse retina," *Free Radical Biology and Medicine* 53(1):64-71, Elsevier, Netherlands (2012).

Spiegel, B.M., et al., "Understanding gastrointestinal distress: a framework for clinical practice," *AM J Gastroenterol* 106(3):380-385, Nature Publishing Group, United States (2011).

Stumpf, J.L, "Deferasirox," *American Journal of Health-System Pharmacy* 64(6):606-616, American Society of Health-System Pharmacists, United States (Mar. 2007).

Thalassemia therapy, Deferasirox and Deferiprone are useful for iron overload in thalassemia major, Medical letter on the CDC & FDA; 88, 3 pages (2006).

Thompson, M.G., et al., "Antibacterial Activities of Iron Chelators Against Common Nosocomial Pathogens," *Antimicrobial Agents and Chemotherapy* 56(10):5419-5421, American Society for Microbiology, United States (Oct. 2012).

Transfusion medicine, Deferiprone shows potential for first-line iron chelation drug obesity, fitness & wellness week; 1498, 3 pages (2005).

Tsou, A.Y., et al., "Pharmacotherapy for Friedreich Ataxia," *CNS Drugs* 23(3):213-223, Springer International, New Zealand (2009).

Venkataram, S and Khohlokwane, M, "Microencapsulation of an Iron Chelator for Sustained Release and Crystal Habit Modification," *Journal of Microencapsulation* 13(5):519-525, Informa Healthcare, United Kingdom (Sep.-Oct. 1996).

Waldmeier, P.C., et al., "Inhibition of Catechol-o-methyltransferase (Comt) as Well as Tyrosine and Tryptophan Hydroxylase by the Orally Active Iron Chelator, 1,2-dimethyl-3-hydroxypyridin-4-one (L1, Cp20), in Rat Brain in Vivo," *Biochemical Pharmacology* 45(12):2417-2424, Elsevier Science, United Kingdom (Jun. 1993).

Ware, H.M. and Kwiatkowski, J.L., "Evaluation and Treatment of Transfusional Iron Overload in Children," *Pediatr Clin N Am* 60:1393-1406, Elsevier, Netherlands (2013).

Weigel, K.J., et al., "Iron chelation and multiple sclerosis," *ASN Neuro* 6(1): 44-63, Sage Publications, United States (2014).

Whiteside, D.P., et al., "Pharmacokinetic Disposition of the Oral Iron Chelator Deferiprone in the Domestic Pigeon (*Columba livia*)," *Journal of Avian Medicine and Surgery* 21(2):121-129, Association of Avian Veterinarians, United States (Jun. 2007).

NCT02728843, "Study of Parkinson's Early Stage with Deferiprone (SKY)", ClinicalTrials.gov, accessed at https://clinicaltrials.gov/ct2/show/NCT02728843?term=02728843&rank=1, accessed on Jan. 4, 2019.

Hoffbrand, A.V., et al., "Role of Deferiprone in chelation therapy for transfusional iron overload," *Blood* 102(1):17-24, American Society of Hematology, United States (2003).

Morales, N.P., et al., "Bioequivalence study of a film-coated tablet of deferiprone in healthy Thai volunteers," *International Journal of Clinical Pharmacology and Therapeutics* 47(5):358-364, American Society of Pharmacology & Therapeutics, United States (2009).

Rujivipat, S., and Bodmeier, R., "Improved Drug delivery to the lower intestinal tract with tablets compression-coated with enteric/nonenteric polymer powder blends," *European Journal of Pharmaceutics and Biopharmaceutics* 76:486-492, Elsevier, Netherlands (2010).

International Search Report and Written Opinion for International Application No. PCT/IB2018/058350, Canadian Intellectual Property Office, Canada, dated Feb. 5, 2019.

"Clinical Trial: Comparison of Deferiprone Delayed Release Tablets and Deferiprone Oral Solution in Healthy Volunteers." Indian eGov Newswire, May 26, 2015. Infotrac Newsstand, http://link.galegroup.com/apps/doc/A414977911/STND?u=tplmain&sid=STND&xid=e7ec89ba.

Office Action dated Feb. 7, 2019, in U.S. Appl. No. 16/171,170, Sherman, B.S., et al., filed Oct. 25, 2018, 11 pages.

Office Action dated Mar. 1, 2019, in U.S. Appl. No. 16/171,170, Sherman, B.S., et al., filed Oct. 25, 2018, 11 pages.

Office Action dated Jul. 16, 2019, in U.S. Appl. No. 16/171,170, Sherman, B.S., et al., filed Oct. 25, 2018, 11 pages.

Office Action dated Aug. 5, 2019, in U.S. Appl. No. 16/171,170, Sherman, B.S., et al., filed Oct. 25, 2018, 11 pages.

Office Action dated Jun. 25, 2020, in U.S. Appl. No. 16/171,170, Sherman, B.C., et al., filed Oct. 25, 2018, 7 pages.

Office Action dated Feb. 21, 2020, in U.S. Appl. No. 16/171,173, Sherman, et al., filed Oct. 25, 2018, 23 pages.

Office Action dated May 13, 2019, in U.S. Appl. No. 16/171,173, Sherman, B.S., et al., filed Oct. 25, 2018, 8 pages.

Clinical Trials, "Comparison of Deferiprone Delayed Release Tablets and Deferiprone Oral Solution in Healthy Volunteers," available at, https://clinicaltrials.gov/ct2/show/NCT02442310?term=NCT02442310&draw=2&rank=1, (last accessed on Jan. 30, 2020), Published May 13, 2016.

Felton, L. (Ed.), "Remington: Essentials of Pharmaceutics," Chapters 2, 30-32 and Appendix B., Pharmaceutical Press, London, UK, (2013).

Hilton, A., et al., "Use of Hydoxypropyl Methylcellulose Acetate Succinate in an Enteric Polymer Matrix to Design Controlled-Release Tablets of Amoxicillin Trihydrate," *Journal of Pharmaceutical Sciences*, 82(7): 737-743, American Pharmaceutical Association, United States (1993).

FERRIPROX® (deferiprone) tablets, for oral use, prescribing information, Oct. 2011, accessed at URL: https://www.accessdata.fda.gov/drugsatfda_docs/label/2011/021825lbl.pdf on Jul. 19, 2019.

Office Action dated Oct. 26, 2021, in U.S. Appl. No. 16/714,520, Sherman, B.C. et al., filed Dec. 13, 2019, 10 pages.

Office Action dated Dec. 8, 2021, in U.S. Appl. No. 16/839,928, Sherman, B.C. et al., filed Apr. 3, 2020, 8 pages.

Office Action dated May 5, 2022, in U.S. Appl. No. 16/714,520, Sherman, B.C. et al., filed Dec. 13, 2019, 7 pages.

* cited by examiner

DELAYED RELEASE DEFERIPRONE TABLETS AND METHODS OF USING THE SAME

REFERENCE TO RELATED APPLICATIONS

The present application is a continuation of U.S. patent application Ser. No. 17/327,135, filed on May 21, 2021, which is a continuation of U.S. patent application Ser. No. 16/714,520, filed on Dec. 13, 2019, which is a continuation of U.S. patent application Ser. No. 16/171,170, filed on Oct. 25, 2018, which claims priority to U.S. Provisional Application Nos. 62/577,055, filed on Oct. 25, 2017, and 62/596,043, filed on Dec. 7, 2017, each of which is incorporated herein by reference in its entirety.

BACKGROUND

Deferiprone is an iron chelator, used in the treatment of generalized iron overload, particularly in conditions where frequent blood transfusions lead to iron overload including, e.g., thalassemia (Renzo Galanello, Ther Clin Risk Manag. 2007 Oct;3(5):795-805), Sickle Cell Disease (Ware and Kwiatkowski, Pediatr Clin North Am. 2013 Dec;60(6):1393-406) and Myelodysplasia (Sheth, Curr Opin Hematol. 2014 May;21(3):179-85) (each incorporated herein by reference in its entirety). Deferiprone is also used in conditions of localized tissue or cellular iron overload, even in the absence of generalized iron overload, such as neurodegenerative diseases where cellular iron mishandling is a prominent feature including, e.g., Friedreich's Ataxia, Parkinson's disease, Pantothenate Kinase-Associated Neurodegeneration (PKAN) and other forms of neurodegeneration with brain iron accumulation (NBIA), Multiple Sclerosis, Age-Related Macular Degeneration and Superficial Siderosis. See Kakhlon et al., Can J Physiol Pharmacol. 2010 Mar;88(3):187-96, Cabantchik et al., Front Pharmacol. 2013 Dec; 4:167, Cossu et al., Parkinsonism. Relat Disord., 2014 Jun;20(6):651-4, Weigel et al., ASN Neuro. 2014 Jan;6(1), Song et al., Free Radic Biol Med. 2012 Jul;53(1):64-71, and Levy and Llinas, Stroke. 2012 Jan;43(1):120-4 (each incorporated herein by reference in its entirety).

Deferiprone is sold in the U.S. and elsewhere as an Immediate Release (IR) 500 mg tablet, for example, under the trade name Ferriprox®, which is also available as an IR 1000 mg tablet and a liquid formulation of 100 mg/mL in some jurisdictions.

BRIEF SUMMARY

Certain aspects of this disclosure are directed to a delayed release tablet comprising deferiprone for oral administration to a human subject, wherein twice daily administration of the delayed release tablet is bioequivalent in the steady state to the same daily dose of an immediate release tablet comprising deferiprone administered three times daily.

In another aspect, the disclosure is directed to a tablet for oral administration of an active pharmaceutical ingredient (in particular, deferiprone) to a human subject, wherein the tablet comprises: (a) a core comprising the active pharmaceutical ingredient in a therapeutically effective amount and an enteric polymer, and (b) an enteric coating, wherein the tablet is scored such that it can be administered as a whole tablet or a half tablet and wherein if the tablet is administered as one or more half tablets, the half tablets are bioequivalent to the whole in, e.g., a single dose study, in a fasted state, a fed state, or both.

In another aspect, the disclosure is directed to a tablet for oral administration of an active pharmaceutical ingredient comprising: (a) a core comprising the active pharmaceutical ingredient in a therapeutically effective amount and an enteric polymer, and (b) an enteric coating, the tablet being scored to facilitate breakage into half tablets, wherein both the whole and the half tablets display a delayed release dissolution profile.

In another aspect, the disclosure is directed to a tablet for oral administration comprising: (a) a core comprising deferiprone in a therapeutically effective amount and an enteric polymer; and (b) an enteric coating comprising an enteric polymer, wherein the tablet is suitable for twice daily dosing.

In another aspect, the disclosure is directed to a tablet comprising deferiprone for twice daily oral administration to a human subject, wherein a single dose of the tablet provides a mean $AUC_\infty/C_{max}$ ratio between 3.5 hours and 6.0 hours in both fasted and fed state.

In another aspect, the disclosure is directed to a tablet for oral administration comprising: (a) a core comprising 1000 mg or 600 mg of deferiprone, an enteric polymer, a pH adjusting agent, a glidant, and a lubricant; and (b) an enteric coating comprising a plasticizer, a diluent, an anti-tacking agent, and an enteric polymer, the tablet being a whole tablet which is scored to facilitate breakage of the tablet into half tablets.

In another aspect, the disclosure is directed to a method for treating a subject with iron overload or a neurodegenerative disease (e.g., Huntington's disease or amyotrophic lateral sclerosis), comprising orally administering to the subject in need thereof a deferiprone tablet (e.g., a delayed release tablet) disclosed herein.

In certain aspects, the disclosure is directed to a method of treating Huntington's disease in a subject in need thereof comprising administering a composition comprising deferiprone to the subject.

In certain aspects, the disclosure is directed to a method of treating amyotrophic lateral sclerosis (ALS) in a subject in need thereof comprising administering a composition comprising deferiprone to the subject. Some embodiments are directed to methods of reducing or slowing the progression of a disability associated with ALS. In some embodiments, the subject is further administered riluzole.

In certain aspects, the disclosure is to directed to a method of treating a human subject with iron overload comprising orally administering to the subject in need thereof 3000 mg/day deferiprone, wherein the subject is administered the deferiprone two times per day.

In certain aspects, the disclosure is to directed to a method of treating a human subject with iron overload comprising orally administering to the subject in need thereof 1200 mg/day deferiprone, wherein the subject is administered the deferiprone two times per day.

DESCRIPTION OF THE INVENTION

I. Definitions

Figure 1:
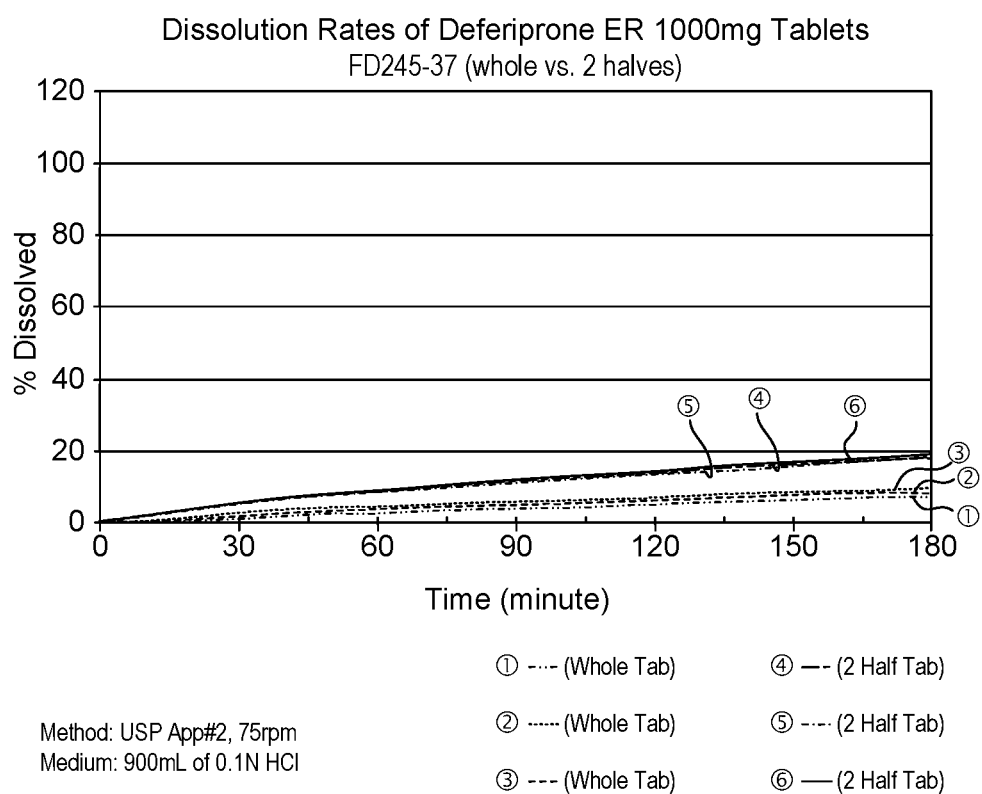
FIG. 1 shows the dissolution of whole and half delayed release (DR) tablets in 0.1N HCl, reflecting dissolution in stomach acid.

As used herein, the indefinite articles "a" or "an" should be understood to refer to "one or more" of any recited or enumerated component. For example, "a tablet" refers to one or more tablets.

Also as used herein, "and/or" refers to and encompasses any and all possible combinations of one or more of the associated listed items, as well as the lack of combinations when interpreted in the alternative ("or").

When the term "about" is used in conjunction with a numerical value or range, it modifies that value or range by extending the boundaries above and below the numerical values set forth. The term "about" is used herein to modify a numerical value above and below the stated value by a variance of 10 percent, up or down (higher or lower), i.e., ±10%, unless a different variance is indicated (e.g., ±30%, ±20%, ±5%, ±1%, etc.).

Wherever aspects are described herein with the language "comprising," otherwise analogous aspects described in terms of "consisting of" and/or "consisting essentially of" are also provided. To the extent that the term "includes" or "including" is used in the specification or the claims, it is intended to be inclusive in a manner similar to the term "comprising" as that term is interpreted when employed as a transitional word in a claim.

"Deferiprone" as used herein refers to deferiprone or a pharmaceutical acceptable salt thereof.

The term "pharmaceutically acceptable salt" of a given compound refers to salts that retain the biological effectiveness and properties of the given compound, and which are not biologically or otherwise undesirable. "Pharmaceutically acceptable salts" include, for example, salts with inorganic acids and salts with an organic acid. Salts of deferiprone can include pharmaceutically acceptable salts, especially salts with bases, such as appropriate alkali metal or alkaline earth metal salts, e.g., sodium, potassium or magnesium salts, pharmaceutically acceptable transition metal salts, such as zinc salts, or salts with organic amines, such as cyclic amines, such as mono-, di- or tri-lower alkylamines, such as hydroxy-lower alkylamines, e.g., mono-, di- or trihydroxy-lower alkylamines, hydroxy-lower alkyl-lower alkylamines or polyhydroxy-lower alkylamines. Cyclic amines are, e.g., morpholine, thiomorpholine, piperidine or pyrrolidine. Suitable mono-lower alkylamines are, e.g., ethyl- and tert-butylamine; di-lower alkylamines are, e.g., diethyl- and diisopropylamine; and tri-lower alkylamines are, e.g. trimethyl- and triethylamine. Appropriate hydroxy-lower alkylamines are, e.g., mono-, di- and triethanolamine; hydroxy-lower alkyl-lower alkylamines are, e.g., N,N-dimethylamino- and N,N-diethylaminoethanol; a suitable polyhydroxy-lower alkylamine is, e.g., glucosamine.

"Core" or "tablet core" as used herein comprises an active ingredient, e.g., deferiprone, and one or more excipients compressed into an uncoated tablet. The core can be coated with various coatings, including an enteric coating.

"Delayed release" or "DR" as used herein refers to protecting an active ingredient, e.g., deferiprone, from rapid release at acidic pH, e.g., in the stomach at least in the fasted state, while enabling the active ingredient to be released at a higher rate at a higher pH, e.g., in the intestines. In some embodiments, DR will be understood to mean that, when tested in USP apparatus 2 at 75 rpm, the extent of dissolution will be under 20% at 1 hour in 0.1N HCl, and the rate of dissolution will be substantially higher (e.g., over 30%, e.g. over 40%, in 1 hour) in phosphate buffer with pH 6.8 than the rate of dissolution in 0.1N HCl.

"Disintegrant" as used herein refers to an excipient that is insoluble in water, but swells when wetted to cause a tablet to disintegrate.

"Dissolution" as used herein refers to the process by which a solute forms a solution in a solvent.

"Enteric coat" or "enteric coating" as used herein refers to a coating comprising an enteric polymer. An enteric coating can serve to prevent or delay a tablet's dissolution or disintegration in a gastric environment.

"Enteric coated tablet" means a tablet having a core comprising an active ingredient, which is coated with an enteric coating.

"Enteric polymer" as used herein is understood to mean a polymer that is relatively insoluble at the acidic pH of the fasted stomach (e.g., about pH 1 to about pH 4), but soluble at higher pH (e.g., about pH 4.5 to about pH 8), which corresponds to the pH in the small intestine or thereafter, particularly in the duodenum or ileum.

"Fasted state" as used herein refers to abstinence from food for a defined period of time after a meal (typically, at least several hours, e.g., 4 or 6 hours, after a meal).

"Fed state" as used herein refers to administration with a meal or soon after a meal (e.g., within about 1 hour).

"Gastric distress" as used herein refers to discomfort of the gastrointestinal (GI) tract, e.g., one or more of pain, cramping, bloating, nausea, indigestion, heartburn, and gas.

"Half tablet" as used herein means either of the two parts of a tablet obtained by splitting the tablet into two parts of equal or approximately equal weight. In some embodiments, a half tablet is from about 40% to about 60% by weight of the whole tablet from which the half was derived. In some embodiments, the approximately equal weight of each half tablet is about 45-55% of the total weight of the whole tablet.

"Percent" or "%" as used herein refers to weight percentage (w/w) unless otherwise specified.

"Scored tablet" as used herein refers to a tablet that is debossed with one or more lines, also known as a "score line", to facilitate splitting the tablet, e.g., to enable administration of a half tablet. In some embodiments, the tablet can be scored with two, three, four, or more score lines.

"Tablet" as used herein refers a solid oral pharmaceutical dosage form. In some embodiments, the tablet is a compressed tablet.

"Whole tablet" means a complete tablet, i.e., not broken or split into parts.

Terms such as "treating" or "treatment" or "to treat" or "ameliorating" or "alleviating" or "to alleviate" can refer to both 1) therapeutic measures that cure, slow down, lessen symptoms of, reverse, and/or halt progression of a diagnosed pathologic condition or disorder and 2) prophylactic or preventative measures that prevent, reduce the incidence of, reduce the risk of, and/or slow the development of a targeted pathologic condition or disorder. Thus, those in need of treatment include those who already have the disorder; those prone to developing the disorder; and those in whom the disorder is to be prevented. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those who already have the condition or disorder as well as those prone to developing the condition or disorder or those in which the condition or disorder is to be prevented or incidence reduced.

By "subject" or "individual" or "patient," is meant any human subject, for whom diagnosis, prognosis, treatment, or therapy is desired.

By "therapeutically effective dose or amount" or "effective amount" is intended an amount of active pharmaceutical ingredient, e.g., deferiprone, that when administered brings about a positive therapeutic response with respect to treatment of or reducing the risk of a disease in a subject to be treated.

It will be understood that the deferiprone IR tablets used as the "reference" or "reference product" herein are Ferriprox® IR tablets (500 mg) as approved by FDA and sold in the United States. For instance, the "reference" or "reference product" herein may be a Ferriprox® IR tablet with (1) a core containing 500 mg deferiprone, microcrystalline cellulose, colloidal silicon dioxide, and magnesium stearate; and (2) a coating containing hydroxypropyl methyl cellulose, polyethylene glycol, and titanium dioxide.

II. Tablets

In certain aspects, the application is directed to a delayed release tablet comprising deferiprone in its core. Delayed release, e.g., provided by enteric coating, serves to delay dissolution of an active ingredient, e.g., deferiprone, from a tablet core. In some embodiments, delayed release is desirable either in the case of a medicinal ingredient that causes gastric irritation if released in the fasted stomach, and/or in the case of a medicinal ingredient that is acid labile and would thus degrade if released in the fasted stomach.

Some pharmaceutical tablets for oral administration are coated with an enteric coat to provide delayed release. Some other pharmaceutical tablets for oral administration are debossed with a score line, to make it easy for the patient to break the tablets into two approximately equal parts to enable administration of half tablets, e.g., for dosing flexibility. However, it is difficult to combine both features into a single tablet; that is, to produce a tablet that is enteric coated but can be broken into two parts without destroying the delayed release feature. This is because the surface at the interface of a broken tablet is no longer protected by the enteric coating. This results in at least the following problems: (1) If the unprotected core disintegrates and/or dissolves quickly, the dissolution of the broken tablet in the stomach acid will be faster than the whole tablet, so that protection against gastric irritation will be lost; (2) Alternatively, if the unprotected core tablet disintegrates and/or dissolves slowly enough to prevent gastric irritation even without the protection of the enteric coating, then dissolution and absorption in the intestines can also be relatively slow, causing a reduction of extent of absorption and/or peak serum levels; and (3) The broken tablet no longer delivers the drug at the same rate and possibly the same extent as the unbroken tablet. These problems can contribute to half tablets not being bioequivalent to whole tablets. For example, Iranian patent application 90-07-27-71996 discloses a formulation of deferiprone that is enteric coated. It discloses protecting against gastric distress by using a methacrylic acid copolymer to enteric-coat the deferiprone tablet, wherein the coating is about 7.4% of the total weight of the tablet (800 mg core tablet containing 500 mg of deferiprone). The enteric coated tablet formulation disclosed in Iranian patent application 90-07-27-71996 loses the enteric coating benefit when the tablets are bisected or halved. The EC tablet from Iranian patent application 90-07-27-71996 (Avicenna Lab) included a core tablet of 500 mg deferiprone, 290 mg microcrystalline cellulose, 1 mg colloidal silicon dioxide, and 9 mg magnesium stearate (800 mg total core weight); and a coating of 34.68 mg methacrylic acid copolymer, 15.56 mg talc, 3.61 mg PEG 6000, 4.38 mg titanium dioxide, 4.93 mg hypromellose, 6 cm Poaz, and 0.82 mg sodium bicarbonate (63.98 mg total weight of coating). The weight of the coating is about 7.4% of the total weight of the EC tablet. In certain embodiments, the tablets of the current application differ from the EC tablet from Iranian patent application 90-07-27-71996. For example, in some embodiments, the DR tablets disclosed herein do not include 290 mg microcrystalline cellulose, 1 mg colloidal silicon dioxide, and/or 9 mg magnesium stearate (800 mg total core weight); and some embodiments, the coating of the DR tablets disclosed herein do not include 34.68 mg methacrylic acid copolymer, 15.56 mg talc, 3.61 mg PEG 6000, 4.38 mg titanium dioxide, 4.93 mg hypromellose, 6 cm Poaz, and/or 0.82 mg sodium bicarbonate (63.98 mg total weight of coating). Furthermore, in certain embodiments, the weight of the coating of the DR tablets disclosed herein is not about 7.4% of the total weight of the EC tablet.

In certain aspects, the present disclosure is directed to a composition, e.g., a tablet, comprising deferiprone for oral administration to a human subject. In one embodiment, the composition is a tablet for oral administration comprising (a) a core comprising deferiprone and (b) an enteric coating. Preferably, the tablet is designed to release deferiprone in the post-stomach portions of the gastrointestinal (GI) tract. In some embodiments, the tablet does not substantially disintegrate in the stomach or at least in the fasted stomach, i.e., the tablet substantially does not dissolve until the tablet reaches the intestine. In some embodiments, at least 75%, at least 80%, at least 85%, at least 95%, at least 99%, or 100% of the tablet disintegrates in the intestine.

In some embodiments, the tablet is administered as a whole tablet. In some embodiments, the tablet is scored for administration of about half the dosage of the whole tablet. In some embodiments, the tablet is administered as a half tablet. In some embodiments, the tablet is administered as one or more whole tablets in combination with one or more half tablets.

In certain aspects, a tablet of the present disclosure is formulated to have relatively little (e.g., less than 20%), if any, dissolution in the fasted stomach, but will more rapidly dissolve in the intestines, and thus can be referred to as a delayed release composition. In some embodiments, a tablet of the present disclosure confers a similar rate of dissolution with half and whole tablets, independent of the pH of the dissolving media. In some aspects, a tablet of the present disclosure embraces the attributes of an enteric coated tablet, without its deficiencies, so that tablets can be halved, to enable fine tuning of the dosing to administer whole tablets, half tablets or any combination thereof. Half tablets of the disclosure resist dissolution in acidic media (0.1 N HCl), representing the fasted stomach contents, as do whole tablets; and, at a higher pH, representing the contents of the small intestine, also exhibit a rate of dissolution similar to whole tablets.

In some embodiments, the enteric coating is between about 1-20%, 1-15%, 1-10%, about 1-9%, about 1-8%, about 1-7%, about 1-6%, about 1-5%, about 1-4%, about 1-3%, about 1-2%, about 0.5-5%, or about 0.5-2% of the total weight of the tablet. In some embodiments, the coating is less than 7%, less than 6%, less than 5%, less than 4%, less than 3%, less than 2.5%, less than 2.4%, less than 2.3%, less than 2.2.%, less than 2.1% or less than 2% of the total weight of the tablet; and/or the coating is more than 1% of the total weight of the tablet. In some embodiments, the coating is about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, or about 3.0%, or a range between any two of the preceding values, e.g., 1.0-1.8%, 1.0-2.0%, 1.0-2.4%, 1.2-1.7%, 1.5-2.0%, 2.0-2.5%, 2.2-2.7%, or 2.5-3.0% of the total weight of the tablet. In some embodiments, the coating is about 1.5% of the total weight of the tablet. In other embodiments, the coating is about 2.5% of the total weight of the tablet.

III. Core

The present disclosure is directed to a composition, e.g., a delayed release tablet, comprising a core comprising an active pharmaceutical ingredient, e.g., deferiprone or a pharmaceutically acceptable salt thereof.

In some embodiments, the tablet core comprises between about 100 mg to about 1500 mg, between about 250 mg to about 1250 mg, or between about 900 mg to about 1100 mg of deferiprone. In some embodiments, the tablet comprises about 100 mg, about 200, about 250 mg, about 300 mg, about 400 mg, about 500 mg, about 600 mg, about 700 mg, about 750 mg, about 800 mg, about 900 mg, about 1000 mg, about 1100 mg, about 1200 mg, about 1300 mg, about 1400 mg, or about 1500 mg of deferiprone. In certain embodiments, the tablet comprises about 1000 mg of deferiprone.

In some embodiments, the active pharmaceutical ingredient, e.g., deferiprone, is about 75-95% (e.g., 80-95% or 85-95%) of the total core weight. In some embodiments, the active agent, e.g., deferiprone, is about 85%, about 86%, about 87%, about 88%, about 89%, about 90%, about 91%, about 92%, about 93%, about 94%, or about 95% of the total core weight.

In some embodiments, the tablet core of one DR tablet for once, twice, or three times daily dosing comprises at least about 200 mg, at least about 300 mg, at least about 400 mg, at least about 500 mg, or at least about 600 mg of deferiprone. In some embodiments, the tablet core of one DR tablet for once, twice, or three times daily dosing comprises at least about 600 mg of deferiprone. In some embodiments, the tablet core of one DR tablet for once, twice, or three times daily dosing comprises at least about 500 mg of deferiprone. In some embodiments, the tablet core comprises between about 200 mg to about 1500 mg, about 300 mg to about 900 mg, about 300 mg to about 700 mg, about 500 mg to about 700 mg, about 500 mg to 1500 mg, about 500 mg to 750 mg, about 900 mg to about 1100 mg, about 300 mg, about 400 mg, about 500 mg, about 600 mg, about 750 mg, about 800 mg, about 1000 mg, about 1200 mg, about 1250 mg, or about 1500 mg of deferiprone. In some embodiments, tablet cores comprising 600 mg or 1000 mg of deferiprone are preferred.

In some embodiments, the tablet core of one DR tablet for once, twice, or three times daily dosing comprises at least about 200 mg, at least about 300 mg, or at least about 400 mg of deferiprone. In some embodiments, the tablet core of one DR tablet for once, twice, or three times daily dosing comprises about 200 mg to about 500 mg, about 200 mg to about 400 mg, about 200 mg, about 300 mg, about 400 mg, or about 500 mg of deferiprone. In some embodiments, the tablet core of one DR tablet for twice daily dosing comprises at least about 500 mg of deferiprone. In some embodiments, the tablet core comprises between about 200 mg to about 1500 mg, about 300 mg to about 900 mg, about 300 mg to about 600 mg, about 300 mg to about 500 mg, about 500 mg to 1500 mg, about 500 mg to 750 mg, about 900 mg to about 1100 mg, about 600 mg, about 750 mg, about 800 mg, about 1000 mg, about 1200 mg, about 1250 mg, or about 1500 mg of deferiprone.

In some embodiments, the tablet core comprises an enteric polymer as an excipient. Prior to the present application, when an enteric coated tablet was broken, e.g., in half at the score line, the surface at the interface of the broken score line, e.g., of the two halves, was no longer protected by the enteric coating. In some embodiments, including an enteric polymer in the core helps maintain a relatively low dissolution rate in 0.1 N HCl for a split tablet, e.g., a half tablet, thus limiting dissolution in the fasted stomach, while still enabling faster dissolution at intestinal pH.

In some embodiments, the enteric polymer is between about 1% to 20%, 1% to 15%, 1% to 10%, or 1% to 5% by weight of the core. In some embodiments, the enteric polymer is about 1%, about 1.5%, about 2%, about 2.5%, about 3%, about 3.5%, about 4%, about 4.5%, about 5%, about 5.5%, about 6%, about 6.5%, or about 7% by weight of the core, or a range between any two of the preceding values, e.g., about 2-2.5%, 2.5-3%, 3-3.5%, 3.5-4%, 4-4.5%, or 4.5-5% by weight of the core. In some embodiments, the enteric polymer is about 2.5% by weight of the core. In some embodiments, the enteric polymer is about 4.5% by weight of the core.

In some embodiments, the enteric polymer in the core is selected from the group consisting of hydroxypropyl methylcellulose (HPMC), acetate succinate (i.e., HPMCAS), HPMC phthalate, polyvinyl acetate phthalate, methacrylic acid copolymers, a derivative thereof, and a combination thereof. In some embodiments, the enteric polymer in the core is HPMCAS.

In some embodiments, the tablet core of a tablet, e.g., a delayed release tablet, disclosed herein includes between about 900 mg to about 1100 mg of deferiprone and between about 10 mg to about 80 mg, between about 20 mg to about 80 mg, between about 20 mg to about 60 mg, between about 20 mg to about 50 mg, between about 20 mg to about 40 mg, between about 25 mg to about 35 mg of an enteric polymer, e.g., HPMCAS. In some embodiments, the tablet core of a tablet, e.g., a delayed release tablet, disclosed herein includes between about 500 mg to about 750 mg of deferiprone and between about 10 mg to about 80 mg, between about 20 mg to about 80 mg, between about 20 mg to about 60 mg, between about 20 mg to about 50 mg, between about 20 mg to about 40 mg, between about 25 mg to about 35 mg of an enteric polymer, e.g., HPMCAS. In some embodiments, the tablet core of a tablet, e.g., a delayed release tablet, disclosed herein includes between about 400 mg to about 800 mg of deferiprone (e.g., about 600 mg) and between about 10 mg to about 80 mg, between about 20 mg to about 80 mg, between about 20 mg to about 60 mg, between about 20 mg to about 50 mg, between about 20 mg to about 40 mg, or between about 25 mg to about 35 mg of an enteric polymer, e.g., HPMCAS.

In some embodiments, the tablet core of a tablet, e.g., a delayed release tablet, disclosed herein includes between about 200 mg to about 500 mg of deferiprone and between about 10 mg to about 80 mg, between about 20 mg to about 80 mg, between about 20 mg to about 60 mg, between about 20 mg to about 50 mg, between about 20 mg to about 40 mg, between about 25 mg to about 35 mg of an enteric polymer, e.g., HPMCAS.

In some embodiments, the tablet core of a tablet, e.g., a delayed release tablet, disclosed herein includes about 1000 mg of deferiprone and about 30 mg of an enteric polymer, e.g., HPMCAS. In particular, the tablet core of the tablet includes 1000 mg of deferiprone and 28.5 mg of HPMCAS.

In some embodiments, the tablet core of a tablet, e.g., a delayed release tablet, disclosed herein includes about 600 mg of deferiprone and about 30 mg of an enteric polymer, e.g., HPMCAS. In particular, the tablet core of the tablet includes 600 mg of deferiprone and 29.5 mg of HPMCAS.

In some embodiments, the tablet core of a tablet, e.g., a delayed release tablet, disclosed herein includes between about 400 mg of deferiprone and about 20 to about 30 mg of an enteric polymer, e.g., HPMCAS. In some embodiments, the tablet core of a tablet, e.g., a delayed release tablet, disclosed herein includes about 600 mg of deferiprone and about 20 mg to about 30 mg of an enteric polymer, e.g., HPMCAS.

In some embodiments, the core comprises one or more basic excipients. In some embodiments, the basic excipient is selected from the group consisting of meglumine, metal oxides, metal hydroxides, basic salts of weak acids, and a combination thereof. Metal oxides include, but are not limited to, magnesium oxide, aluminum oxide, and zinc oxide. Metal hydroxides include, but are not limited to, sodium hydroxide, potassium hydroxide, magnesium hydroxide, and calcium hydroxide. Basic salts of weak acids include, but are not limited to, sodium or potassium salts of carbonate, bicarbonate, acetate, and citrate. In certain embodiments, the basic excipient is magnesium oxide, meglumine or a combination thereof. In some embodiments, the basic excipient is magnesium oxide.

In some embodiments, the basic excipient is about 1-10%, about 1-5%, about 1-4%, about 2-8%, about 2-6%, about 2-5%, about 2-4%, about 3-5%, about 3-4%, or about 4-5% of the total weight of the core. In some embodiments, the tablet core of a tablet, e.g., a delayed release tablet, disclosed herein includes magnesium oxide in an amount of about 3%, about 4%, or about 5% of the total weight of the core. In some embodiments, the basic excipient is about 4.5% of the total weight of the core. In some embodiments, the basic excipient is about 3.7% of the total weight of the core.

In some embodiments, the tablet core of a tablet, e.g., a delayed release tablet, disclosed herein comprises about 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 90 mg, or 100 mg of a basic excipient, or a range between any two of the preceding values, e.g., about 5-100 mg, 5-80 mg, 10-60 mg, 40-60 mg, or 20-30 mg of a basic excipient.

In some embodiments, the tablet core of a tablet, e.g., a delayed release tablet, disclosed herein includes about 1000 mg of deferiprone and about 50 mg of a basic excipient, e.g., magnesium oxide. In some embodiments, the tablet core of a tablet, e.g., a delayed release tablet, disclosed herein includes about 600 mg of deferiprone and about 25 mg of a basic excipient, e.g., magnesium oxide. In some embodiments, the tablet core of a tablet, e.g., a delayed release tablet, disclosed herein includes about 400 mg of deferiprone and about 10 to about 20 mg of a basic excipient, e.g., magnesium oxide.

In some embodiments, the tablet core does not comprise a disintegrant.

In some embodiments, the tablet core is coated with an enteric coating described herein. In some embodiments, the core comprises the same or a different enteric polymer than the enteric polymer in the coating.

In some embodiments, the core is at least 90%, at least 91%, at least 92%, at least 93%, at least 94%, at least 95%, at least 96%, at least 97%, at least 98%, or at least 99% of total tablet weight.

In some embodiments, other excipients included in the tablet core are selected from fillers, binders (e.g., to increase tablet hardness), lubricants such as magnesium stearate (e.g., to prevent sticking to the tooling during compression into tablets), glidants such as colloidal silicon dioxide (e.g., to improve flow in the tableting process), and combinations thereof.

In some embodiments, the core comprises a glidant such as, for example, colloidal silicon dioxide. In some embodiments, the glidant is about 1%, 0.5%, 0.45, 0.4%, 0.35%, 0.3%, 0.25%, 0.2%, 0.1% by weight of the core, or a range between any two of the preceding values, e.g., about 0.2-0.5%, 0.2-0.4%, 0.2-0.3%, 0.3-0.5%, 0.3-0.4%, or 0.4-0.5% by weight of the core. In some embodiments, the core comprises about 0.45% by weight of a glidant (e.g., colloidal silicon dioxide). In some embodiments, the core comprises about 0.3% by weight of a glidant (e.g., colloidal silicon dioxide).

In some embodiments, the tablet core of a tablet, e.g., a delayed release tablet, disclosed herein includes about 1000 mg of deferiprone and about 5 mg of a glidant, e.g., colloidal silicon dioxide. In some embodiments, the tablet core of a tablet, e.g., a delayed release tablet, disclosed herein includes about 600 mg of deferiprone and about 2 mg of a glidant, e.g., colloidal silicon dioxide. In some embodiments, the tablet core of a tablet, e.g., a delayed release tablet, disclosed herein includes about 400 mg of deferiprone and about 1 mg to about 2 mg of a glidant, e.g., colloidal silicon dioxide.

In some embodiments, the core comprises a lubricant such as, for example, magnesium stearate, calcium stearate, stearic acid, sodium stearyl fumarate, or talc. In some embodiment, the core comprises magnesium stearate as a lubricant.

In some embodiments, the lubricant is about 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% by weight of the core, or a range between any two of the preceding values, e.g., 0.5-1%, 0.5-2%, 0.6-2%, 0.7-2%, 1-1.5%, 1.2-1.7%, or 1.5-2% by weight of the core. In some embodiments, the core comprises about 0.6% by weight of a lubricant (e.g., magnesium stearate). In some embodiments, the core comprises about 1.5% by weight of a lubricant (e.g., magnesium stearate).

In some embodiments, the tablet core of a tablet, e.g., a delayed release tablet, disclosed herein comprises about 2 mg, 3 mg, 4 mg, 5 mg, 7 mg, 8 mg, 9 mg, 10 mg, 11 mg, 12 mg, 13 mg, 14 mg, 15 mg, 16 mg, 17 mg, 18 mg, 19 mg, 21 mg, 22 mg, 23 mg, 24 mg, or 25 mg of a lubricant, or a range between any two of the preceding values, e.g., about 2-25 mg, 2-10 mg, 2-8 mg, 2-6 mg, 7-20 mg, 10-20 mg, or 15-20 mg of a lubricant.

In some embodiments, the tablet core of a tablet, e.g., a delayed release tablet, disclosed herein includes about 1000 mg of deferiprone and about 17 mg of a lubricant, e.g., magnesium stearate. In some embodiments, the tablet core of a tablet, e.g., a delayed release tablet, disclosed herein includes about 600 mg of deferiprone and about 4 mg of a lubricant, e.g., magnesium stearate. In some embodiments, the tablet core of a tablet, e.g., a delayed release tablet, disclosed herein includes about 400 mg of deferiprone and about 1 mg to about 4 mg of a lubricant, e.g., magnesium stearate.

In some embodiments, the core comprises HPMC acetate succinate, magnesium oxide, colloidal silicon dioxide, magnesium stearate, and about 1000 mg of deferiprone.

In some embodiments, the core comprises HPMC acetate succinate, magnesium oxide, colloidal silicon dioxide, magnesium stearate, and about 600 mg of deferiprone.

In some embodiments, the core comprises HPMC acetate succinate, magnesium oxide, colloidal silicon dioxide, magnesium stearate, and about 400 mg of deferiprone.

IV. Enteric Coating

In certain aspects of the disclosure, the composition, e.g., a tablet, can comprise an enteric coating. Such a coating can serve to reduce gastric irritation. The enteric coating can delay the dissolution from the tablets core until the tablet reaches the intestine. The present disclosure is directed to a composition, e.g., a delayed release tablet, comprising a core comprising an active pharmaceutical ingredient, e.g., deferiprone or a pharmaceutically acceptable salt thereof, and an enteric coating.

Suitable enteric polymers for the enteric coating include, e.g., hydroxypropyl methylcellulose acetate succinate (also referred to as hypromellose acetate succinate or HPMCAS), HPMC phthalate (also referred to as hypromellose phthalate), polyvinyl acetate phthalate, cellulose acetate phthalate, cellulose acetate trimellitate, shellac, zein, methacrylic acid copolymers (e.g., methacrylic acid copolymer Type C Dispersion 30%), derivatives thereof, and combinations thereof.

In some embodiments, the preferred enteric polymers in the enteric coating are HPMC acetate succinate and methacrylic acid copolymers, e.g., methacrylic acid copolymer type C in aqueous dispersion.

In some embodiments, the enteric polymer in the coating is about 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.5%, 3%, 3.5%, or 4%, by weight of the tablet, or a range between any two of the preceding values, e.g., 0.5-1%, 0.5-2%, 0.5-3%, 0.5-4%, 0.6-1%, 0.6-2%, 0.6-3%, 0.6-4%, 0.7-1%, 0.7-2%, 0.7-3%, 0.7-4%, 1-1.5%, 1.1-1.7%, 1-2%, 1.5-2%, 1-3%, 1-3.5%, or 1-4%, by weight of the tablet. In some embodiments, the enteric polymer in the coating (e.g., methacrylic acid copolymer) is about 0.8% by weight of tablet. In some embodiments, the enteric polymer in the coating (e.g., methacrylic acid copolymer) is about 1.4% by weight of the tablet (e.g., methacrylic acid copolymer).

In some embodiments, the enteric coating comprises about 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 16 mg, 17 mg, 18 mg, 19 mg, 20 mg, 25 mg, or 30 mg of an enteric polymer, or a range between any two of the preceding values, e.g. about 5-20 mg, 7-20 mg, 7-30 mg, 8-15 mg, or 8-10 mg of an enteric polymer.

In some embodiments, a tablet, e.g., a delayed release DR tablet, disclosed herein includes about 1000 mg of deferiprone and about 9 mg of an enteric polymer in the coating, e.g., methacrylic acid copolymer (from about 31 mg of dispersion). In some embodiments, the tablet core of a tablet, e.g., a delayed release tablet, disclosed herein includes about 600 mg of deferiprone and about 9 mg of an enteric polymer in the coating, e.g., methacrylic acid copolymer (from about 31 mg of dispersion). In some embodiments, the tablet core of a tablet, e.g., a delayed release tablet, disclosed herein includes about 400 mg of deferiprone and about 9 mg of an enteric polymer in the coating, e.g., methacrylic acid copolymer (from about 31 mg of dispersion).

In some embodiments, the enteric coating comprises, in addition to the enteric polymer, other excipients, including for example, a plasticizer, a lubricant or anti-tack agent such as talc, an opacifier, a colorant, a diluent, or any combination thereof.

In some embodiments, the enteric coating plasticizer is diethyl phthalate, citrate esters (e.g., triethyl citrate), polyethylene glycol, glycerol, acetylated glycerides, acetylated citrate esters, dibutyl sebecate, castor oil, or any combination thereof.

In some embodiments, the enteric coating comprises about 0.5 mg, 0.6 mg, 0.7 mg, 0.8 mg, 0.9 mg, 1 mg, 1.1 mg, 1.2 mg, 1.3 mg, 1.4 mg, 1.5 mg, 2 mg, 2.5 mg, 3 mg, 3.5 mg, 4 mg, 4.5 mg, or 5 mg of a plasticizer, or a range between any two of the preceding values, e.g. about 0.5-5 mg, 0.7-2 mg, or 0.8-1.2 mg of a plasticizer.

In some embodiments, the enteric coating comprises a diluent (e.g., lactose, sucrose, fructose, mannitol, and the like, or combinations thereof). In some embodiments, the enteric coating comprises talc as the lubricant or anti-tack agent.

Certain aspects of the application are directed to a composition (e.g., delayed release tablet) comprising a core comprises 1000 mg of deferiprone, an enteric polymer, a pH adjusting agent, a glidant, and a lubricant; and a coating comprises a plasticizer, a diluent, an anti-tacking agent, and an enteric polymer. In some embodiments, the core comprises 1000 mg of deferiprone, HPMCAS-LF, Magnesium oxide, Colloidal Silicon Dioxide, Magnesium stearate; and the coating comprises Triethyl Citrate, Sucrose, Talc, and Methacrylic Acid Copolymer Dispersion. In a further embodiment, the composition (e.g., delayed release tablet) core comprises 1000 mg of deferiprone, 28 mg HPMCAS-LF, 50 mg Magnesium oxide, 4.8 mg (2.6 mg+2.2 mg) Colloidal Silicon Dioxide, 17.2 mg Magnesium stearate; and the coating comprises 1.03 mg Triethyl Citrate, 3.09 mg Sucrose, 3.09 mg Talc, and 31 mg Methacrylic Acid Copolymer Dispersion.

Certain aspects of the application are directed to a composition (e.g., delayed release tablet) comprising a core comprises 600 mg of deferiprone, an enteric polymer, a pH adjusting agent, a glidant, and a lubricant; and a coating comprises a plasticizer, a diluent, an anti-tacking agent, and an enteric polymer. In some embodiments, the core comprises 600 mg of deferiprone, HPMCAS-LF, Magnesium oxide, Colloidal Silicon Dioxide, and Magnesium stearate; and the coating comprises Triethyl Citrate, Sucrose, Talc, and Methacrylic Acid Copolymer Dispersion. In a further embodiment, the core comprises 600 mg of deferiprone, 29.5 mg HPMCAS-LF, 24.5 mg Magnesium oxide, 2 mg (1 mg+1 mg) Colloidal Silicon Dioxide, and 4 mg Magnesium stearate; and the coating comprises 1.03 mg Triethyl Citrate, 3.09 mg Sucrose, 3.09 mg Talc, and 31 mg Methacrylic Acid Copolymer Dispersion.

In some embodiments, the core comprises 600 mg of deferiprone, Hypromellose Acetate Succinate AS-LF, Magnesium oxide light, Colloidal Silicon Dioxide, and Magnesium stearate; and the coating comprises Triethyl Citrate, Sucrose, Talc, Methacrylic Acid Copolymer Dispersion, and Titanium Dioxide. In a further embodiment, the core comprises 600 mg of deferiprone, 29.5 mg Hypromellose Acetate Succinate AS-LF, 24.5 mg Magnesium oxide light, 2 mg (1 mg+1 mg) Colloidal Silicon Dioxide, and 4 mg Magnesium stearate; and the coating comprises 1.032 mg Triethyl Citrate, 3.09 mg Sucrose, 2.09 mg Talc, 30.96 mg Methacrylic Acid Copolymer Dispersion, and 8.5 mg Titanium Dioxide.

In some embodiments, the enteric coating is between about 1-20%, 1-15%, 1-10%, about 1-9%, about 1-8%, about 1-7%, about 1-6%, about 1-5%, about 1-4%, about 1-3%, about 1-2%, about 0.5-5%, or about 0.5-2% of the total weight of the tablet. In some embodiments, the coating is less than 7%, less than 6%, less than 5%, less than 4%, less than 3% or less than 2% of the total weight of the tablet. In some embodiments, the enteric coating is between 0.5% and 5% of the total tablet weight. In some embodiments, the enteric coating is between 0.5% and 3% of the total tablet weight. In some embodiments, the enteric coating is between 0.5% and 2% of the total tablet weight. In some embodiments, the enteric coating is between 0.5% and 1.5% of the total tablet weight. In some embodiments, the coating is about 1%, about 1.5%, about 2%, about 2.5%, about 3%, about 3.5%, about 4%, about 4.5%, about 5%, about 5.5%, or about 6% of the total weight of the tablet.

In some embodiments, the coating is about 1.5% of the total weight of the tablet. In some embodiments, the coating is about 2.5% of the total weight of the tablet.

In some embodiments, a tablet, e.g., a delayed release tablet, disclosed herein includes about 1000 mg of deferiprone and about 1.5% of an enteric coating by weight of the tablet. In some embodiments, a tablet, e.g., a delayed release tablet, disclosed herein includes about 600 mg of deferiprone and about 2.5% of an enteric coating by weight of the tablet.

Another aspect of the disclosure is directed to a method for delayed release of deferiprone in a human subject comprising administering a tablet of the disclosure to the subject, wherein the tablet comprises a core and an enteric coating as disclosed herein and is administered as a whole tablet, a half tablet, or a combination thereof.

Another aspect of the disclosure is directed to a method for reducing gastric distress in a human subject in need of deferiprone treatment comprising administering a tablet of the disclosure to the subject, wherein the tablet comprises a core and an enteric coating as disclosed herein and the tablet is administered as a whole tablet, a half tablet, or a combination thereof.

V. Dosing

The present disclosure provides dosing regimens useful for the methods of using the pharmaceutical compositions, e.g., delayed release tablets, described herein. In some embodiments, a deferiprone composition of the disclosure is administered to a subject in need thereof once, twice, or three times daily. In particular, the deferiprone composition of the disclosure is administered to a subject in need thereof twice daily.

In some embodiments, the subject in need thereof suffers from iron overload (e.g., transfusional iron overload, e.g., in subjects suffering from thalassemia, myelodysplasia, or sickle cell disease). In some embodiments, the subject in need thereof suffers from a neurodegenerative disease (e.g., Parkinson's disease, amyotrophic lateral sclerosis (ALS), Huntington's disease, Friedreich's Ataxia, Pantothenate Kinase Associated Neurodegeneration (PKAN), or neurodegeneration with brain iron accumulation (NBIA)).

In some embodiments, the subject in need thereof suffers from iron overload that is transfusional iron overload. In certain aspects, the subject suffers from transfusional iron overload and whose prior chelation therapy is inadequate. In certain aspects, the subject suffers from transfusion iron overload and has a cardiac MM T2* of 20 ms or less (e.g., 10 ms).

In some embodiments, the pharmaceutical composition is for oral delivery, e.g., a tablet of the disclosure.

In some aspects, a DR deferiprone composition (in particular, tablet compositions) of the disclosure is administered twice daily. IR deferiprone tablets are inconvenient to patients as they require three times daily dosing (TID dosing). Patients generally prefer a regimen of twice daily (BID) or once daily dosing. One reason that TID dosing has been required is that the elimination half-life of deferiprone is only about 2 hours. After a deferiprone IR tablet is ingested, the deferiprone content is rapidly absorbed from the upper part of the gastrointestinal tract, appearing in the blood within 5 to 10 minutes of oral administration. Peak serum concentrations occur approximately 1 hour after a single dose in fasted healthy subjects and patients, and up to 2 hours after a single dose in the fed state. Because the elimination half-life is short, the serum concentration is reduced to below therapeutically effective levels well before the next dose, if dosing is less frequent than TID.

Another problem associated with IR deferiprone is acute gastric distress, which can persist for days or longer. This is a limiting adverse event for a substantial number of patients, e.g., patients who stop taking the medication in the first few days as a result of the gastric distress and thus forego the benefits of deferiprone.

Extended release (ER) dosage forms have been developed to enable twice daily or once daily dosing for some drugs. Such dosage forms are designed to release the active drug content gradually over an extended period of time, usually about 5 to 10 hours for a dosage form intended for twice daily dosing, and over about 8 to 20 hours for a dosage form intended for once daily dosing. This can generally be done only for drugs that are absorbed throughout the ileum and duodenum, so that the extent of absorption is not compromised by the gradual release as the dosage form passes through the intestines.

An issue with ER dosage forms relates to the maximum (or peak) serum concentration ($C_{max}$). By protracting the period of absorption, e.g., with the use of an extended release formulation, the $C_{max}$ will end up much lower than with the IR tablet. This could be a problem in achieving the desired effects of certain drugs, such as iron chelators, where both the $C_{max}$ and the area under the serum concentration vs. time graph (AUC) can impact the efficacy.

Certain aspects of the present disclosure are directed to a deferiprone tablet for twice daily (BID) dosing that is bioequivalent in the steady state to an IR tablet for TID dosing using the same total daily dosage. In certain embodiments, the BID is bioequivalent in the steady state, wherein after at least three days of dosing, the mean ratio of AUC (over 24 hours) and the mean ratio of Cmax for the tablets for BID dosing relative to the IR tablets for TID is within 80% to 125%. The tablets for twice daily dosing then provide the same chelation benefit to a subject as the IR tablets, yet with certain advantages of the twice daily dosing. In addition to the convenience of BID dosing, this regimen enhances compliance in patients, e.g., those who choose not to bring their mid-day dose to school or work and thus lose the benefit of a full daily dose of deferiprone.

In certain aspects, the disclosed formulations are utilized to target particular serum concentration time profiles and achieve the improved properties disclosed herein.

Certain aspects of the disclosure are directed to overcoming problems associated with TID dosing, without sacrificing the benefits of achieving the $C_{max}$, by providing a tablet for twice daily administration that provides both of the following when compared to an IR tablet administered TID having the same total daily dosage:

i. Similar extent of absorption as IR tablets, and thus similar average serum concentration; and ii. Similar peak serum concentration, but with the peaks occurring twice daily instead of three times daily.

Certain aspects of the disclosure are directed to overcoming problems associated with TID dosing, without sacrificing the benefits of achieving the $C_{max}$, by providing a tablet for twice daily administration that provides both of the following when compared to an IR tablet administered TID having the same total daily dosage:

i. Equivalent extent of absorption as IR tablets, and thus similar average serum concentration; and ii. Equivalent peak serum concentration, but with the peaks occurring twice daily instead of three times daily.

Another aspect of the present disclosure is to provide a tablet formulation comprising deferiprone for twice daily administration that exhibits delayed onset of release as well as lengthening the duration of release, but without affecting the terminal half-life, thus enabling the achievement of peaks and troughs in the serum. This advantage is applied to both whole and half tablets, as the dissolution rate of half tablets is similar to that of whole tablets at all relevant pHs, so that half tablets are bioequivalent to whole tablets in single dose bioequivalence studies, in both the fasted state and the fed state.

Results shown herein also demonstrate that in the steady state, the delayed release tablets of the present disclosure when administered BID were able to achieve the same maximum peak concentrations (Cmax) as IR tablets of Ferriprox®, when the IR tablets were given three times a day, and the total amount absorbed (AUC) was the same for both products over a 24 hour period. Thus, certain benefits of twice daily dosing, and in some instances less gastrointestinal distress, are obtained, without a compromise on efficacy.

"Bioequivalence" refers to the absence of a significant difference between the bioavailability, i.e., the extent of absorption and peak concentration, between two pharmaceutical drug products (e.g., a test product and a reference product) over the course of a period of time, at the same dose and under the same conditions.

The determination of whether or not a test product is bioequivalent to a reference product is determined by performing a study, referred to as a bioequivalence or comparative bioavailability study, in a group of subjects, usually about 18-36 subjects or more, under controlled conditions.

The study can be done in a "crossover" design, which means that the study is done in 2 or more phases, usually at least a week apart, depending in part on the half-life of the drug. In the first phase, half the subjects are randomly assigned to ingest the test product first and the other half ingest the reference product first. In the second phase, each subject ingests the alternate product.

In each phase, blood samples are drawn from each subject, on a predetermined schedule after ingestion of the test product. The blood samples are then analyzed to determine serum concentrations of the drug (test product, e.g., deferiprone) at each time point. The results for each subject, for both the test and reference products, are then compiled to determine the following:

AUC — defined as the area under the curve of serum concentration versus time for a chosen period of time after ingestion, for example, 24 hours.

AUCT or $AUC_T$—defined as the area under the curve of serum concentration versus time from the time of ingestion to the last sampling time.

AUCI or $AUC_I$—defined as the area under the curve of serum concentration versus time from the time of ingestion to time infinity, which is estimated using $AUC_T$ and the terminal elimination rate.

$C_{max}$—defined as the peak serum concentration.

AUC ratio—defined as the ratio of AUC from the test product to AUC from the reference product, calculated for each subject.

$C_{max}$ ratio—defined as the ratio of $C_{max}$ from the test product to $C_{max}$ from the reference product, also calculated for each subject.

Mean AUC ratio—defined as the antilog of the average of the logarithms of AUC ratios for all subjects.

Mean $C_{max}$ ratio—defined as the antilog of the average of the logarithms of $C_{max}$ ratios for all subjects.

An "equivalent extent of absorption" is defined as a mean AUC ratio between 80% and 125% calculated for a test product versus a reference product, in a study usually conducted in 18 or more subjects.

An "equivalent peak concentration" is defined as a mean $C_{max}$ ratio between 80% and 125% calculated for a test product versus a reference product, in a study usually conducted in 18 or more subjects.

Both an equivalent extent of absorption and an equivalent peak concentration must be achieved to be considered bioequivalent.

For any bioavailability parameter, the "true" mean ratio of the parameter as measured in the test product to that as measured in the reference product is defined as the mean ratio that would be found in a study in an infinite number of subjects. As no study can be done in an infinite number of subjects, the mean ratio as determined in any study is only an estimate of the true mean ratio. As the number of subjects in a study is increased, the mean ratio results generally become a better estimate of the true mean ratio. Unless stated otherwise herein, reference to a product having a particular ratio of a parameter to that of a reference product will be understood to mean the mean as determined in a study in at least 18 subjects.

Bioequivalence studies can be conducted as single dose studies, either in the fasted state or the fed state. In a study conducted in the fasted state, the products are ingested without food and usually at least several hours before or after a meal. If a study is conducted in the fed state, the products are ingested with a meal or soon after a meal. In some embodiments, bioequivalence studies can be single-dose or steady state. In a single dose study, each subject receives only one dose of the product being ingested in each phase, although that dose can include more than 1 tablet, depending on the size of the dose being studied. In a steady state study, subjects ingest doses on a dosing schedule regimen being tested (for example, twice or three times daily) for at least several doses until steady state is reached, and then blood samples are taken over a predetermined period, usually over one day. For assessment of modified release formulations, whether delayed release or extended release, a study in the presence of food and following several doses to achieve steady state (to simulate effects during chronic dosing) is often conducted.

The administration of a tablet to a patient who has recently ingested a meal can alter the rate and extent of absorption and, if a medicine is to be taken with a meal, it can be important to characterize the rate and extent of absorption of the delayed release tablet with food, compared to an IR tablet with food.

Bioequivalence studies can also be conducted as multi-dose studies, conducted over at least several days of dosing to determine whether or not two products are bioequivalent in the "steady state", after several days of dosing. "Steady state" as used herein is achieved when the rate of drug input equals the rate of drug elimination, as determined by no further increase in drug concentrations in the subject following the administration of repeated doses. "Bioequivalent in the steady state" will be understood to mean that, after at least three days of dosing of a test product, the mean ratio of AUC (over 24 hours) and the mean ratio of Cmax is within 80% to 125% of those for a reference product.

In some embodiments, the present disclosure provides a composition, e.g., delayed release tablet, for twice daily dosing that is bioequivalent in the steady state to the same daily dose of an IR tablet taken three times daily, e.g., as illustrated in the examples below.

Certain aspects of the disclosure are directed to a tablet for oral administration comprising deferiprone, for which twice daily administration provides equivalent extent of absorption, at least in a steady state study, when compared to the same total daily dosage administered three times daily as IR tablets.

Certain aspects of the disclosure are directed to a tablet for oral administration comprising deferiprone, for which twice daily administration provides equivalent peak serum concentration, at least in a steady state study, when compared to the same total daily dosage administered three times daily as IR tablets.

Certain aspects of the disclosure are directed to a tablet for BID oral administration comprising deferiprone, for which the characteristics of equivalent extent of absorption and/or rate of absorption, as aforesaid, are met for, not only whole tablets, but also for half tablets, so as to allow dosing with half tablets. In some embodiments, the tablets are preferably debossed with a score line, to facilitate breaking into half tablets. For example, if a whole tablet comprises about 1000 mg of deferiprone, such that a half tablet comprises about 500 mg of deferiprone, then a dose of about 1500 mg can be taken as one whole tablet plus one half tablet, and a total daily dose of 3000 mg can be achieved with BID dosing.

In some embodiments, to achieve desired absorption characteristics, tablets of the disclosure are formulated to exhibit desired dissolution rates as shown by in vitro dissolution testing. References to dissolution testing herein can be understood to mean testing in USP apparatus 2, at 75 rpm, in 900 mL of media, i.e., 0.1 N hydrochloric acid (HCl), 0.5 M phosphate buffer at pH 4.5, and 0.5 M phosphate buffer at pH 6.8, unless indicated otherwise. A stated dissolution result is understood to mean the average result of 6 or more tablets.

Certain aspects of the disclosure are directed to a half tablet or whole tablet for oral administration to a human subject, comprising a core comprising deferiprone, for which dissolution at 60 minutes in pH 4.5 is between about 55% and about 90%, between about 60% and about 90%, or between about 65% and about 85%.

Certain aspects of the disclosure are directed to a half tablet or whole tablet for oral administration to a human subject comprising a core comprising deferiprone, for which dissolution at 60 minutes in pH 6.8 is between about 55% and about 90%, between about 60% and about 90%, or between about 65% and about 85%.

In some aspects, approximately 100% of the deferiprone is released within about 90 minutes when measured by USP Apparatus Type II Paddle Method at 75 rpm in 900 mL at pH 6.8 or 4.5. In some aspects, approximately 50% of the deferiprone is released within about 30 minutes when measured by USP Apparatus Type II Paddle Method at 75 rpm in 900 mL at pH 6.8 or 4.5.

Also, certain aspects of the disclosure are directed to a half tablet or whole tablet for oral administration to a human subject comprising a core comprising deferiprone, for which dissolution at 60 minutes in 0.1 N HCl is under 20%, or under 10%.

In some embodiments, a single dose of a tablet of the disclosure provides a mean $AUC_\infty/C_{max}$ ratio between 3.5 hours and 6.0 hours in fasted state when the tablet is administered to human subjects.

In some embodiments, a single dose of a tablet of the disclosure provides a mean $AUC_\infty/C_{max}$ ratio between 3.5 hours and 6.0 hours in fed state when the tablet is administered to human subjects. In some embodiments, the tablet comprises 1000 mg deferiprone. In some embodiments, the tablet comprises 600 mg deferiprone. In some embodiments, the mean $C_{max}$ is between 2.670 and 13.232 µg/mL when the tablet is administered to a human subjects. In some embodiments, the median $T_{max}$ is between 1.33 and 4.00 hours when the tablet is administered to human subjects. In some embodiments, the median $T_{max}$ is between 2.00 and 8.00 hours when the tablet is administered to human subjects. In some embodiments, the median $T_{max}$ is between 1.33 and 6.03 hours when the tablet is administered to human subjects. In some embodiments, the ratio of $AUC_t/C_{max}$ is between 2.858 to 6.596 hours when the tablet is administered to human subjects. In some embodiments, the ratio of $AUC_t/C_{max}$ is between 3.225 to 8.506 hours when the tablet is administered to human subjects.

In some embodiments, the dosing is for treating a subject suffering from iron overload (e.g., transfusional iron overload, e.g., in subjects suffering from thalassemia, myelodysplasia, or sickle cell disease). Certain aspects of the disclosure are directed to dosing regimens useful for the methods of treating iron overload as described herein. In some embodiments of the methods for treating iron overload, the total amount of deferiprone administered per day is about 1 mg/kg/day to about 200 mg/kg/day, about 1 mg/kg/day to about 150 mg/kg/day, about 20 mg/kg/day to about 150 mg/kg/day, about 50 mg/kg/day to about 125 mg/kg/day, or about 50 mg/kg/day to about 100 mg/kg/day. In some embodiments, the administration is one, twice or three times daily. In some embodiments, the dosing for treatment of iron overload is about 1 mg/kg to about 150 mg/kg, about 20 mg/kg to about 150 mg/kg, 25 mg/kg to about 125 mg/kg, or about 50 mg/kg to about 100 mg/kg twice daily (BID).

In some embodiments, the dosing is for treating a subject suffering from a neurodegenerative disease, e.g., Parkinson's disease, amyotrophic lateral sclerosis (ALS), Huntington's disease, Friedreich's Ataxia, Pantothenate Kinase Associated Neurodegeneration (PKAN), or neurodegeneration with brain iron accumulation (NBIA). In some embodiments, a deferiprone composition of the disclosure (IR or DR composition) is administered once, twice, or three times daily to a subject suffering from a neurodegenerative disease, e.g., Parkinson's disease, ALS, Huntington's disease, Friedreich's Ataxia, Pantothenate Kinase Associated Neurodegeneration (PKAN), or neurodegeneration with brain iron accumulation (NBIA). In some embodiments, the subject suffers from ALS. In some embodiments, the subject suffers from Huntington's disease. In some embodiments, the subject suffers from Parkinson's disease.

Certain aspects of the disclosure are directed to dosing regimens useful for the methods of treating a neurodegenerative disease described herein. In some embodiments of the methods for treating a neurodegenerative disease, the total amount of deferiprone administered per day is about 1 mg/kg/day to about 200 mg/kg/day, about 1 mg/kg/day to about 150 mg/kg/day, about 1 mg/kg/day to about 100 mg/kg/day, about 1 mg/kg/day to about 50 mg/kg/day, about 1 mg/kg/day to about 40 mg/kg/day, about 1 mg/kg/day to about 30 mg/kg/day, about 1 mg/kg/day to about 20 mg/kg/day, about 1 mg/kg/day to about 15 mg/kg/day, about 1 mg/kg/day to about 10 mg/kg/day, or about 1 mg/kg/day to about 5 mg/kg/day. In some embodiments, the administration is one, twice or three times daily. In some embodiments, the dosing for treatment of a neurodegenerative disease is about 1 mg/kg to about 100 mg/kg, about 1 mg/kg to about 50 mg/kg, 1 mg/kg to about 40 mg/kg, about 1 mg/kg to about 25 mg/kg, or about 1 mg/kg to about 20 mg/kg two times daily (BID).

In some embodiments of the methods, the amount of deferiprone in the composition (e.g., a tablet) is from about 100 mg to about 1500 mg, from about 200 mg to about 1500 mg, from about 400 mg to about 1500 mg, from about 600 mg to about 1500 mg, from about 800 mg to about 1500 mg, from about 1200 mg to about 1500 mg, from about 200 mg to about 1200 mg, from about 400 mg to about 1200 mg, from about 600 mg to about 1200 mg, from about 800 mg to about 1200 mg, from about 200 mg to about 1000 mg, from about 400 mg to about 1000 mg, from about 600 mg to about 1000 mg, from about 800 mg to about 1000 mg, from about 200 mg to about 800 mg, from about 400 mg to about 800 mg, from about 600 mg to about 800 mg, from about 200 mg to about 600 mg, from about 400 mg to about 600 mg, or from about 200 mg to about 400 mg. In some embodiments of the methods, the amount of deferiprone in the composition (e.g., a tablet) is about 100 mg, about 200 mg, about 300 mg, about 400 mg, about 500 mg, about 600 mg, about 800 mg, about 1000 mg, about 1100 mg, about 1200 mg, about 1300 mg, about 1400 mg, about 1500 mg, or any range of values thereof. In particular, the amount of deferiprone in the composition (e.g., a tablet) is 600 mg or 1000 mg deferiprone. In some embodiments, the amount of deferiprone in the tablet is 1000 mg deferiprone. In some embodiments, the amount of deferiprone in the tablet is 600 mg deferiprone.

In some embodiments of the methods, the total daily dose of deferiprone is from about 100 mg/day to about 3000 mg/day, about 200 mg/day to about 3000 mg/day, from about 400 mg/day to about 2400 mg/day, from about 600 mg/day to about 2400 mg/day, from about 800 mg/day to about 2400 mg/day, from about 1200 mg/day to about 2400 mg/day, from about 1600 mg/day to about 2400 mg/day, from about 1800 mg/day to about 2400 mg/day, from about 2000 mg/day to about 2400 mg/day, from about 400 mg/day to about 2000 mg/day, from about 600 mg/day to about 2000 mg/day, from about 800 mg/day to about 2000 mg/day, from about 1200 mg/day to about 2000 mg/day, from about 1600 mg/day to about 2000 mg/day, from about 1800 mg/day to about 2000 mg/day, from about 400 mg/day to about 1800 mg/day, from about 600 mg/day to about 1800 mg/day, from about 800 mg/day to about 1800 mg/day, from about 1200 mg/day to about 1800 mg/day, from about 1600 mg/day to about 1800 mg/day, from about 400 mg/day to about 1600 mg/day, from about 600 mg/day to about 1600 mg/day, from about 800 mg/day to about 1600 mg/day, from about 1200 mg/day to about 1600 mg/day, from about 400 mg/day to about 1200 mg/day, from about 600 mg/day to about 1200 mg/day, from about 800 mg/day to about 1200 mg/day, from about 400 mg/day to about 800 mg/day, from about 600 mg/day to about 800 mg/day, or from about 400 mg/day to about 600 mg/day. In some embodiments of the methods, the total daily dose of deferiprone is about 200 mg/day, about 400 mg/day, about 600 mg/day, about 800 mg/day, about 1000 mg/day, about 1200 mg/day, about 1400 mg/day, about 1600 mg/day, about 1800 mg/day, about 2000 mg/day, about 2200 mg/day, about 2400 mg/day, about 2600 mg/day, about 2800 mg/day, about 3000 mg/day, or any range of values thereof.

In some embodiments of the methods, the composition (e.g., a tablet) is administered once, twice, or three times a day. In some embodiments, the composition (e.g., a tablet) contains about 100 mg, about 200 mg, about 400 mg, about 600 mg, about 800 mg, about 1000 mg, about 1200 mg, about 1600 mg, about 1800 mg, about 2000 mg, about 2200 mg, or about 2400 mg of deferiprone and is administered once, twice, or three times a day. In some embodiments, the composition (e.g., a tablet) contains about 600 mg of deferiprone and is administered once or twice a day.

In some embodiments, the composition (e.g., a tablet) contains about 100, 200, 300, or 400 mg of deferiprone and is administered once, twice, or three times a day. In some embodiments, the composition (e.g., a tablet) contains about 400 mg of deferiprone and is administered once, twice, or three times a day. In some embodiments, the composition (e.g., a tablet) contains about 500 mg of deferiprone and is administered once, twice, or three times a day. In some embodiments, the composition (e.g., a tablet) contains about 1000 mg of deferiprone and is administered once, twice, or three times a day.

Such embodiments disclosed herein can be used to avoid or reduce the risk of gastric distress and/or to treat iron overload in a subject (e.g., suffering from thalassemia, myelodysplasia, or sickle cell disease) or a neurodegenerative disease (e.g., amyotrophic lateral sclerosis).

VI. Methods of Making

In some embodiments, the pharmaceutical composition is prepared for oral delivery. In some aspects, the disclosure is directed to making a delayed release deferiprone tablet disclosed herein.

In some embodiments, the method for making a delayed release deferiprone tablet comprises (a) mixing deferiprone and one or more excipients; (b) compressing the mixture of (a) into a tablet core; and (c) coating the tablet core with an enteric coating suspension or solution. The method can further comprise (d) scoring the tablet core.

In some embodiments, the method for coating a core with an enteric coating solution or suspension comprises spray coating. In the case of coating by spray coating, the operation can be performed according to general coating methods, e.g., a tablet core is spray-coated with an enteric coating solution or suspension according to, for example, a fluidized bed coating method, a pan coating method, or the like.

In some embodiments, the enteric coating solution or suspension comprises an enteric polymer. In some embodiments, the enteric polymer is about 1-50%, about 1-40%, about 5-40%, or about 5-30% of the enteric coating solution or suspension. In some embodiments, the enteric polymer is about 20-80%, about 25-75%, or about 30-70% of the enteric coating when the coating has dried. In some embodiments, the enteric polymer is about 50-60% by weight of the enteric coating when the coating has dried. In some embodiments, the enteric polymer is about 55% by weight of the enteric coating when the coating has dried.

In some embodiments, the enteric coating suspension or solution comprises a plasticizer such as, e.g., diethyl phthalate, citrate esters (e.g., triethyl citrate), polyethylene glycol, glycerol, acetylated glycerides, glycerin fatty acid ester, cetyl alcohol, stearyl alcohol, acetylated citrate esters, dibutylsebacate, castor oil, or combinations thereof.

In some embodiments, the plasticizer is about 0.1-10%, about 0.1-5%, about 0.5-5%, or about 0.5-2% of the enteric coating suspension or solution. In some embodiments, the plasticizer is about 1-10% or about 4-8% by weight of the enteric coating when the coating has dried. In some embodiments, the plasticizer is about 6% by weight of the enteric coating when the coating has dried.

In some embodiments, the enteric coating suspension or solution comprises a lubricant or anti-tack agent (e.g., talc).

In some embodiments, the lubricant or anti-tack agent is about 0.5-10%, about 0.5-8%, about 0.5-5%, or about 1-5% of the enteric coating suspension or solution. In some embodiments, the lubricant or anti-tack agent is about 10-30% or about 15-25% by weight of the enteric coating when the coating has dried. In some embodiments, the lubricant or anti-tack agent is about 20% by weight of the enteric coating when the coating has dried.

In some embodiments, the enteric coating suspension or solution can further comprise a diluent, e.g., a sugar (e.g., lactose, sucrose, fructose, mannitol and mixtures thereof).

In some embodiments, the diluent is about 0.5-10%, about 0.5-8%, about 0.5-5%, or about 1-5% of the enteric coating suspension or solution. In some embodiments, the diluent is about 10-30% or about 15-25% by weight of the enteric coating when the coating has dried. In some embodiments, the diluent is about 20% by weight of the enteric coating when the coating has dried.

In some embodiments, the enteric coating can be applied as a solution or a latex suspension in organic solvents or aqueous solvents or mixtures thereof. Solvents such as water, lower alcohol, lower chlorinated hydrocarbons, ketones, or mixtures thereof can be used.

In some embodiments, the solvent is about 20-80%, about 30-80%, about 40-80%, or about 50-75% of the enteric coating solution or suspension.

In some embodiments, at least one ionic, nonionic or polymeric surfactant can be added as a stabilizing agent to the enteric coating suspension or solution. Suitable examples of the surfactant include diethanolamine, fatty acids, hydroxypropylmethylcellulose, hydroxypropylcellulose, monoethanolamine, nonoxynol, octoxynol, oleic acid, Poloxamers, polyoxyethylene 50 stearate, polyoxy fatty acids, polyoxyl hydrocarbon ethers, polysorbates (e.g., Polysorbate 80, etc.), povidone, fatty acid salts, sodium lauryl sulfate, sorbitan esters, trolamine and the like, but are not limited to these.

In some embodiments, the enteric coating solution or suspension comprises a plasticizer, a diluent, lubricant or anti-tack agent, and an enteric polymer.

After coating, in some embodiments, an antistatic agent such as talc can be used as well.

By coating a tablet core disclosed herein with a coating layer using the methods disclosed herein, immediate dissolution of the physiologically active substance from the enteric granule at acidic pH (e.g., pH 1 to 4), which corresponds to dissolution in the vicinity of the stomach during the early stage after oral administration, is suppressed, and subsequent dissolution of the physiologically active substance at weakly acidic to weakly alkaline pH (e.g., pH 4.5 to 8), which corresponds to dissolution in the small intestine and thereafter, especially in the duodenum to ileum, is facilitated. In particular, it is possible to more strictly control the dissolution during the early stage after administration.

VII. Methods of Use

The present disclosure provides methods of using the pharmaceutical compositions disclosed herein. In some embodiments, the pharmaceutical composition is for oral delivery. Preferably, the pharmaceutical composition is a tablet for oral delivery. In some embodiments, the pharmaceutical composition is a tablet (e.g., a delayed release tablet disclosed herein).

For example, the most common adverse event with immediate release tablets of deferiprone (Ferriprox®) is that it causes significant gastric distress. Such discomfort can cause patients to refrain from taking the medication, leading to a worsening of their condition. In addition, GI distress can impair health-related quality of life and lead to physical, mental, and social distress. Spiegel, Am J Gastroenterol. 2011 March; 106(3):380-5, incorporated herein by reference in its entirety. In some embodiments, the compositions, e.g., delayed release tablets, of the present disclosure are formulated to reduce gastric distress, a problem that occurs in about 15-30% of patients who begin therapy with deferiprone. In some embodiments, the compositions, e.g., delayed release tablets, disclosed herein have negligible dissolution in the stomach, so as to minimize the gastric distress and yet achieve sufficient rapid dissolution in the intestines to enable the desired rate of release in the intestines. In some embodiments, the compositions, e.g., delayed release tablets, disclosed herein have negligible dissolution in the stomach, so as to minimize the gastric distress and yet achieve similar, but not identical serum concentration time profiles, in vivo, as immediate release tablets of deferiprone, with the addition of a lag time of about one hour.

Certain embodiments of the disclosure are directed to a method for reducing gastric distress in a human subject in need of deferiprone treatment comprising administering a tablet (e.g., a scored delayed release deferiprone tablet) disclosed herein (e.g., a whole tablet, a half tablet, or a combination thereof).

Certain embodiments of the disclosure are directed to a method for delayed release of deferiprone in a human subject comprising administering a tablet disclosed herein (e.g., a whole tablet, a half tablet, or a combination thereof). Certain embodiments of the disclosure are directed to a method of treating a medical condition in a human subject, e.g., where deferiprone is desired, comprising administering a tablet (e.g., a scored delayed release deferiprone tablet) disclosed herein (e.g., a whole tablet, a half tablet, or a combination thereof).

The compositions, e.g., delayed release tablets, of the present disclosure can be particularly useful in patients requiring blood transfusions for survival, such as Hemoglobinopathies, including Thalassemia and Sickle Cell Disease, or patients who have a secondary destruction of their red blood cell forming capability, such as those with Myelodysplasia.

Deferiprone immediate release tablets (Ferriprox®) are currently used to minimize the toxicity of high concentrations of iron in the body, tissues or cells. Thalassemia is a form of inherited autosomal recessive blood disorder characterized by abnormal formation of hemoglobin. The abnormal hemoglobin results in inadequate oxygen transport and an accelerated rate of destruction of red blood cells. People with thalassemia make less hemoglobin and have fewer circulating red blood cells than normal, which results in moderate to severe anemia. Patients require life-long blood transfusions to treat their thalassemia, typically every 2-4 weeks, and each blood transfusion results in an increase of iron into the body, equivalent to the amount that is normally absorbed from food in the gut over 6 months. Since there is no excretory pathway for iron, this excess will cause iron overload, particularly in the liver and other more sensitive tissues with resultant endocrine disorders and iron-induced cardiovascular illness.

Iron overload occurs in sickle cell disease (SCD) patients who require regular chelation therapy. Voskaridou et al., Ann Hematol. 2005 July; 84(7):434-40, incorporated herein by reference in its entirety. Although Sickle Cell Disease is a different hemoglobinopathy, patients with Sickle Cell Disease who require blood transfusions to survive also suffer from iron-toxicity. This is also the case in patients with Myelodysplasia who require repeated blood transfusions.

In some embodiments, the medical condition treated by a composition, e.g., a delayed release tablet, of the present disclosure is iron overload. In some aspects, the medical condition treated by a composition, e.g., a delayed release tablet, is transfusional iron overload in a subject whose prior chelation therapy is inadequate. In some aspects, the medical condition treated by a composition, e.g., a delayed release tablet, is transfusional iron overload in a subject who has a cardiac MRI T2* of 20 ms or less (e.g. 10 ms). In some embodiments, the medical condition treated by a composition, e.g., a delayed release tablet, of the present disclosure is in transfused patients with thalassemia. In some embodiments, a composition, e.g., a delayed release tablet, of the present disclosure is used for treating transfusional iron overload in patients with Sickle Cell Disease. In some embodiments, a tablet (e.g., a scored delayed release deferiprone tablet) of the present disclosure is used for treating transfusional iron overload in patients with Myelodysplasia.

The compositions, e.g., delayed release tablets, of the present disclosure can also be particularly useful in patients with neurodegenerative disease such as Parkinson's disease, amyotrophic lateral sclerosis (ALS), or Huntington's disease because the tablets are not dissolved in the stomach, thus in some instances minimizing the gastric distress, accompanied by nausea and vomiting, that is prominent in patients who start deferiprone. Equally important, the DR tablets of the present disclosure are less rapidly absorbed than IR tablets and other known deferiprone tablets, leading to less nausea and vomiting, where that may be contributing to the GI distress. Yet, the DR tablets of the present disclosure are sufficiently rapidly absorbed after reaching the duodenum, to enable ready penetration into the brain, thereby enabling deferiprone to exhibit its beneficial effects in Parkinson's disease, ALS, Huntington's disease and other neurodegenerative diseases where localized accumulation of iron contributes to the pathology of the disease.

Parkinson's disease is a degenerative disorder of the central nervous system. The motor symptoms of Parkinson's disease result from the death of dopamine-generating cells in the substantia nigra, a region of the midbrain. Early in the course of the disease, the most obvious symptoms are movement-related, e.g., shaking, rigidity, slowness of movement and difficulty with walking and gait. Later in the course of the disease, thinking and behavioral problems can arise, with dementia commonly occurring in the advanced stages of the disease, and depression is the most common psychiatric symptom. Other symptoms include sensory, sleep and emotional problems. Parkinson's disease is more common in older people, with most cases occurring after the age of 50.

The pathology of Parkinson's disease is characterized by the accumulation of a protein called alpha-synuclein into inclusions called Lewy bodies in neurons, along with insufficient formation and activity of dopamine produced in certain neurons within parts of the midbrain. The anatomical distribution of the Lewy bodies is often directly related to the expression and degree of the clinical symptoms of each individual. Diagnosis of typical cases is mainly based on symptoms, with tests such as neuroimaging being used for confirmation.

Early motor symptoms of the disease are commonly managed through the treatment with L-DOPA and dopamine agonists. As the disease progresses and dopaminergic neurons continue to be lost, these drugs eventually become ineffective at treating the symptoms and at the same time produce a complication called dyskinesia, marked by involuntary writhing movements. Diet and exercise and some forms of rehabilitation have shown some effectiveness in alleviating symptoms. Surgery and deep brain stimulation have been used to reduce motor symptoms as a last resort in severe cases where drugs are ineffective. There is no cure for Parkinson's disease.

Huntington's disease is a progressive brain disorder cause by a defective gene (HTT) on chromosome 4 that codes for a protein called huntingtin. The defect causes expansion of CAG (cytosine-adenine-guanine) triplet repeats in the gene coding huntingtin which damages cells in the brain. A diagnostic genetic test for the defective huntingtin gene is available.

Symptoms of Huntington's disease usually develop between ages 30 and 50 and include uncontrolled movement of the arms, legs, head, face and upper body. Huntington's disease also causes a decline in thinking and reasoning skills, including memory, concentration, judgment and ability to plan and organize. Huntington's disease brain changes lead to obsessive-compulsive thoughts and actions and alterations in mood, such as depression, anxiety, anger and irritability.

There is no cure for Huntington's disease, and treatments focus on managing Huntington's disease symptoms. For example, antipsychotic drugs such as olanzapine are used to treat chorea (involuntary movements), antipsychotic drugs or selective serotonin reuptake inhibitors are used to treat irritability, and selective serotonin reuptake inhibitors are used to treat obsessive-compulsive thoughts or actions.

Amyotrophic lateral sclerosis (ALS) is a disease that causes death of the neurons which control voluntary muscles. ALS is also known as Lou Gehrig's disease or motor neurone disease (MND). ALS is characterized by stiff muscles, muscle twitching, and gradual weakening of the muscles due decreased muscle size. This results in difficulty speaking, swallowing and eventually breathing. The cause is not known in 90-95% of ALS cases, while about 5-10% of ALS cases are genetically inherited. ALS diagnosis is based on a person's signs and symptoms with testing done to rule out other potential causes.

There is no cure for ALS. Non-invasive ventilation may improve quality and length of life. Riluzole, a sodium channel blocking drug, can delay the onset of ventilator dependence or tracheostomy and may increase survival by approximately 2-3 months. However, the average survival from onset to death is typically 2-4 years.

In some embodiments, the medical condition treated by a composition, e.g., a tablet (e.g., a scored delayed release deferiprone tablet), disclosed herein is a neurodegenerative disease. In some embodiments, the neurodegenerative disease is Parkinson's disease, amyotrophic lateral sclerosis (ALS), Huntington's disease, Pantothenate-Kinase-associated neurodegeneration, or Friedreich's Ataxia.

Accordingly, certain embodiments of the disclosure are directed to methods for treating a neurodegenerative disease comprising a composition described herein. In some embodiments, the neurodegenerative disease is Parkinson's disease, amyotrophic lateral sclerosis (ALS), Huntington's disease, Friedreich's Ataxia, Pantothenate Kinase Associated Neurodegeneration (PKAN), or neurodegeneration with brain iron accumulation (NBIA). Some embodiments are directed to methods of reducing or slowing progression of a disability associated with ALS. In some embodiments, the subject is further administered riluzole. In some embodiments, the deferiprone is administered prior to, after or at the same time as the riluzole is administered to the subject. In some embodiments, the total daily dose of riluzole is about 20 mg/day to about 500 mg/day.

In some embodiments, the composition is a tablet, a delayed release tablet, a scored delayed release tablet, a whole tablet, a half tablet, or a combination thereof. In some embodiments, the composition is administered by a dosing regimen described herein. In some embodiments, the composition is administered in a fasted state or a fed state.

Certain aspects of the disclosure are directed to a method for treating a human subject with iron overload, comprising orally administering to the subject in need thereof 3000 mg/day or 1200 mg/day deferiprone, wherein the subject is administered the deferiprone two times per day. In some embodiments, the subject suffers from thalassemia or myelodysplasia. In some embodiments, the subject suffers from a neurogenic disease. In some embodiments, the 3000 mg/day deferiprone is administered at a dose of 1500 mg two times a day (e.g., one and a half 1000 mg DR tablets; or three half 1000 mg DR tablets). In some embodiments, the subject exhibits a $C_{max}$ of 48.5-10.5 µg/mL at steady state. In some embodiments, the subject exhibits an AUC$_{(0-24)}$ of 75-95 µg·h/mL at steady state. In some embodiments, the 1200 mg/day deferiprone is administered at a dose of 600 mg two times a day. In some embodiments, the 1200 mg/day deferiprone is administered at a dose of 1200 mg one time per day. In some embodiments, the subject exhibits a $C_{max}$ of 4.00 to 13.558 µg/mL after administration of 600 mg deferiprone in the fed state. In some embodiments, the subject exhibits a $C_{max}$ of 5.880 to 13.690 µg/mL after 600 mg deferiprone in the fasted state. In some embodiments, the subject exhibits a $T_{max}$ of 1.333 to 8.000 hours after administration of 1200 mg deferiprone. In some embodiments, the subject exhibits a AUC$_T$/$C_{max}$ of 3.265 to 6.765 hr after administration of 1200 mg deferiprone.

In some embodiments of these methods, the subject suffers from Parkinson's disease. In some embodiments of these methods, the subject suffers from Huntington's disease. In some embodiments of these methods, the subject suffers from amyotrophic lateral sclerosis (ALS).

VIII. Bioavailability

Pharmacokinetic (PK) parameters (e.g., $C_{max}$, $T_{max}$, AUCT, AUCI, $K_{el}$, $T_{1/2}$) can be assessed for subjects administered a tablet disclosed herein. In some embodiments, the PK parameters are determined by a single dose study. In some embodiments, the PK parameters are determined in a multi-dose or steady state study.

In certain embodiments, a tablet disclosed herein, provides a mean AUC$_\infty$/$C_{max}$ ratio between 3.5 hours and 6.0 hours in single dose bioequivalence studies in both fasted and fed state when the tablet is administered as a whole tablet and when administered as half tablet.

While the present application has been illustrated by the description of embodiments thereof, and while the embodiments have been described in detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples and apparatuses without departing from the spirit or scope of the general inventive concept.

EXAMPLES

The working of the invention might be better understood from the following examples, which are intended to be illustrative and not limiting of the scope of the invention.

Example 1: Preparation of Enteric Coated Delayed Release Tablets

TABLE 1

Deferiprone Delayed Release Tablet (1000 mg and 600 mg)

| Component | Function | Amount (1000 mg) mg | % | Amount (600 mg) mg | % |
|---|---|---|---|---|---|
| Deferiprone | Active | 1000 | 89.6 | 600 | 88.7 |
| HPMCAS-LF | Enteric polymer | 28 | 2.51 | 29.5 | 4.36 |
| Magnesium oxide | pH adjusting agent | 50 | 4.48 | 24.5 | 3.62 |
| Colloidal Silicon Dioxide (part 1) | Glidant | 2.6 | 0.23 | 1 | 0.15 |
| Subtotal Post Compaction | | 1080.6 | 96.8 | 655 | 96.8 |
| Magnesium stearate | Lubricant | 17.2 | 1.54 | 4 | 0.59 |
| Colloidal Silicon Dioxide (part 2) | Glidant | 2.2 | 0.20 | 1 | 0.15 |
| Total | | 1100 | 98.5 | 660 | 97.6 |
| Coating | | | | | |
| Triethyl Citrate | Plasticizer | 1.03 | 0.09 | 1.03 | 0.15 |
| Sucrose | Diluent | 3.09 | 0.28 | 3.09 | 0.46 |
| Talc | Anti-tacking agent | 3.09 | 0.28 | 3.09 | 0.46 |
| *Methacrylic Acid Copolymer Dispersion | Enteric polymer | 31 | 0.83# | 31 | 1.37# |
| **Purified Water | | 124 | — | 126.8 | — |
| TOTAL COATED TABLET | | 1116.5 | 100 | 676.5 | 100 |

*Contains 30% solids.
**Evaporates during the coating process.
The weight percentage of methacrylic acid copolymer in the coating when the coating has dried.

To prepare the tablet core, deferiprone, HPMCAS, magnesium oxide, and colloidal silicon dioxide (part 1) were mixed together, and the mixture was compacted and milled into granules. Magnesium stearate and colloidal silicon dioxide (part 2) were added to and mixed with the granules, and the resulting mixture was compressed into core tablets of about 1100 mg or about 660 mg weight on capsule-shape tooling, bisected on both sides.

The enteric coating suspension was sprayed onto the deferiprone core tablets in a side-vented coating pan until the tablets had a targeted weight gain of approximately 1.5% for the 1000 mg tablets and 2.5% for the 600 mg tablets. The resulting delayed release tablet was designed to have negligible dissolution in the stomach, but rapidly dissolve in the duodenum, for preventing gastric distress. These properties apply to the whole tablet and the half tablet.

Example 2: Dissolution Characteristics of Delayed Deferiprone Tablet (Whole and Half)

The dissolution characteristics of the 1000 mg delayed release deferiprone tablet prepared in Example 1 was tested in vitro using both whole and half tablets.

Dissolution testing was performed in USP apparatus 2, at 75 rpm, in 900 mL of 0.1 N hydrochloric acid (HCl), 0.5 M phosphate buffer at pH 4.5, and 0.5 M phosphate buffer at pH 6.8. The 1000 mg tablets of Example 1 showed the following dissolution characteristics for both whole tablets and half tablets:

Dissolution was below 20% at 180 minutes in 0.1 N HCl [FIG. 1].

Figure 2:
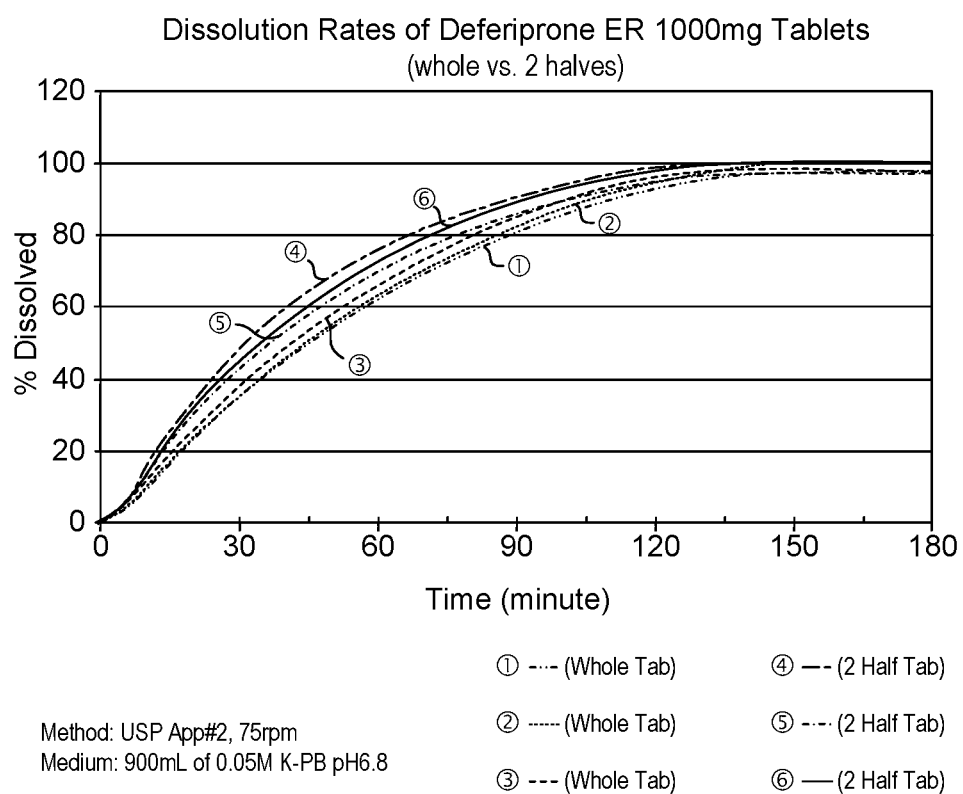
FIG. 2 shows the dissolution of whole and half DR tablets in pH 6.8, reflecting dissolution in the jejunum and ileum.

Dissolution was above 60% at 60 minutes in pH 6.8 [FIG. 2].

Figure 3:
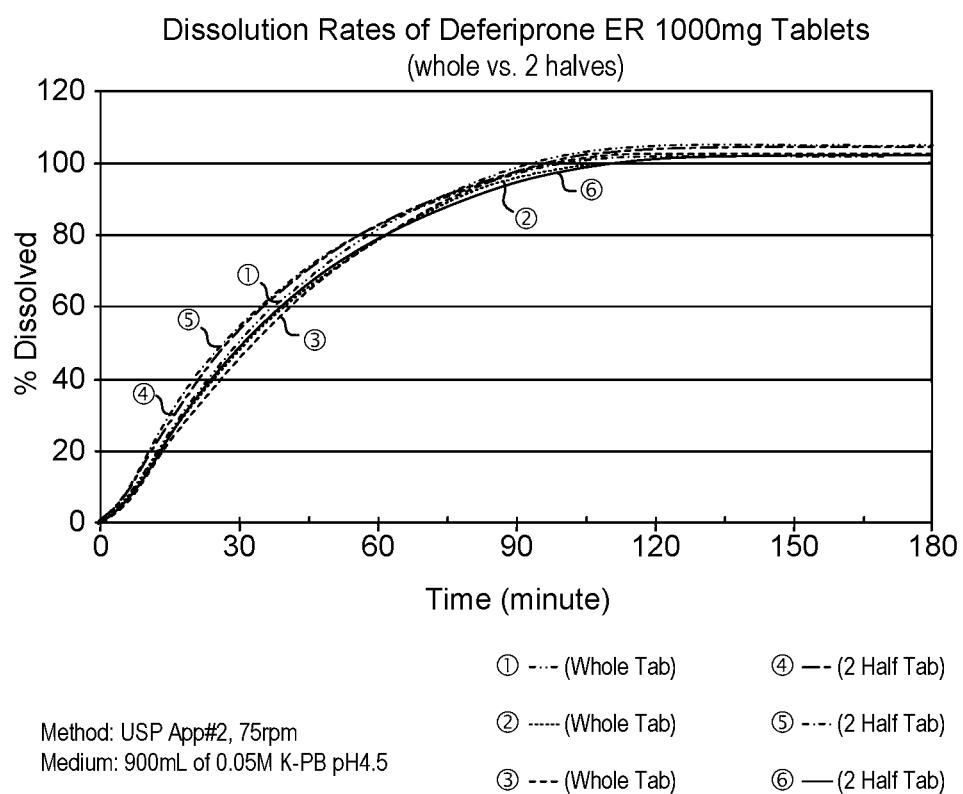
FIG. 3 shows the dissolution of whole and half DR tablets in pH 4.5, reflecting dissolution in the duodenum.

Dissolution was above 80% at 60 minutes in pH 4.5 [FIG. 3].

Example 3: Comparison of Dissolution Rates for Delayed Release vs. Enteric Coated Deferiprone Tablets The dissolution profile for the whole and half delayed release 1000 mg tablet prepared in Example 1 were compared to the dissolution profile for whole and half enteric coated (EC) tablets (Avicenna Lab, Iranian Pat. Appl. No. 90-07-27-71996).

The EC tablet (Avicenna Lab) used for comparison included a core tablet of 500 mg deferiprone, 290 mg microcrystalline cellulose, 1 mg colloidal silicon dioxide, and 9 mg magnesium stearate (800 mg total core weight). The EC tablet (Avicenna Lab) also included a coating of 34.68 mg methacrylic acid copolymer, 15.56 mg talc, 3.61 mg PEG 6000, 4.38 mg titanium dioxide, 4.93 mg hypromellose, 6 cm Poaz, and 0.82 mg sodium bicarbonate (63.98 mg total weight of coating). The weight of the coating is about 7.4% of the total weight of the EC tablet.

Dissolution testing was carried out in a USP Apparatus II at 75 rpm using 900 mL of 0.1N HCl for 180 minutes. Samples were collected at 5 minute intervals to characterize the dissolution profile of the tablets.

In sum, the whole and half delayed release deferiprone tablets from Example 1 had dissolution below 20% at 60, 90, 120, 150, and 180 minutes in 0.1 N HCl (representing the pH of the stomach). No dissolution in 0.1 N HCl was observed for the whole EC tablet (Avicenna Lab), but rapid and complete dissolution were observed in buffered solutions: 95% dissolved at 30 min in a pH 4.5 solution; 94% dissolved at 30 min in a pH 6.0 solution; and 88% dissolved at 30 min in a pH 6.8 solution. However, the half EC tablets (Avicenna Lab) rapidly dissolve, thus losing their enteric coating properties.

Thus, the delayed release formulation of Example 1 demonstrated an advantage over other enteric-coated tablets of deferiprone. In particular, the 1000 mg delayed release tablet of Example 1 exhibits a delayed release in a milieu, representing the pH of stomach acid, but has attributes beyond that provided by an enteric coating. Specifically, the new delayed release tablet of the invention confers a similar rate of dissolution with half and whole tablets, independent of the pH of the dissolving media. That is, the delayed release tablet embraces certain attributes of an enteric coated tablet, without its deficiencies, so that tablets can be halved to enable fine tuning of the dosing to administer half tablets.

Examples 4-5: 24 Hour Bioequivalence Studies

Examples 4-5 relate to bioequivalence studies in human subjects, using the 1000 mg delayed release tablet of deferiprone in Example 1 and Ferriprox® IR tablets.

The first study (Example 4) was a single dose study, which showed a delay in the absorption of the DR tablets, but not an increase in the terminal half-life, and also that half tablets had a similar rate and extent of absorption as whole tablets, whether or not they were administered with food.

The second study (Example 5) was a multiple dose study of equivalent daily doses of DR and IR tablets. This study showed that at steady state, the DR tablets were bioequivalent in the steady state to the IR tablets.

Example 4: Single Dose Pharmacokinetic Study of Deferiprone Delayed Release Tablets Under Fasting and Fed Conditions Versus Ferriprox® Immediate Release Tablets Under Fed Conditions in Healthy Volunteers This was a randomized, single dose, open-label, 4-period, 4-sequence crossover study in healthy male and female volunteers. Subjects were randomized to receive single doses of the following treatments in different sequences, with a 7-day washout period between drug administrations:

One intact 1000 mg tablet of deferiprone DR under fasting conditions (n=23);

One intact 1000 mg tablet of deferiprone DR under fed conditions (n=21);

Two half-tablets (total 1000 mg) of deferiprone DR under fed conditions (n=26); and Two 500 mg tablets of Ferriprox® IR formulation under fed conditions (n=24).

The objectives of the study were to evaluate the effect of food on the PK profile of a single dose of deferiprone DR, to compare the PK profile of the half-tablets to that of the intact tablet, to compare the PK profile of deferiprone DR to that of Ferriprox® IR, and to evaluate the safety and tolerability of a single dose of deferiprone DR.

The main PK parameters of this study are shown in Table 2, and the relative bioavailability is shown in Table 3. Under fed conditions, the time ($T_{max}$) to reach the maximum serum concentration ($C_{max}$) of deferiprone was longer with the DR formulation (3.00 hours) compared with the IR formulation (1.33 hours). The $C_{max}$ for the DR formulation was about 65% of that for the IR formulation. Post-absorption serum drug levels declined at similar rates, with a half-life of approximately 1.8 hours for both formulations. Moreover, there was no significant difference in extent of exposure (AUC) to the drug between the two formulations.

When the DR tablet was administered as half tablets, neither $C_{max}$ nor AUC differed significantly from whole tablet values. With respect to the effect of food, the bioavailability of the DR formulation was the same whether it was administered under fasting or fed conditions. Since the same total dose was given for the DR and IR tablets, it was expected that the $C_{max}$ would be higher for the IR tablets. However, these results provided evidence that 50% more deferiprone in a DR tablet could be given to achieve the same $C_{max}$ as the IR tablet.

For each subject of the pharmacokinetic study, the ratio of $AUC_{0-inf}$ over $C_{max}$ was calculated (Table 4). The resulting ratio was transformed by determining the natural logarithm of the ratio. The mean of the logarithmically transformed ratios across the subjects in the study was calculated and the mean log value was subsequently inversely transformed to the normal scale by determining the anti-logarithm of the mean value.

riprox®) IR tablets at steady state in 35 healthy volunteers. Subjects were randomized to receive the following two treatments, separated by 5 days of washout:

Treatment A: Deferiprone DR, 1500 mg (one and a half 1000 mg tablets) every 12 hours (BID) (total of 3000 mg/day) for 3 days, administered under fed conditions; and Treatment B: Ferriprox® IR, 1000 mg (two 500 mg tablets) every 8 hours (TID) (total of 3000 mg/day) for 3 days, administered under fed conditions.

After appropriate screening and baseline testing, subjects were administered deferiprone BID or TID, as applicable, on Days 1-3. Following a washout period, they returned to the site in the evening of Day 8 and received the other treatment over Days 9-11 and checked out in the morning of Day 12.

For each period, blood samples for pharmacokinetic (PK) assessment were taken prior to the first dose of the day on the first two days of dosing (Days 1-2 and Days 9-10), and

TABLE 2

Summary of Pharmacokinetic Parameters

| Parameter (units) | Deferiprone DR, fasting | Deferiprone DR, fed | Deferiprone DR half-tablets, fed | Deferiprone IR, fed |
|---|---|---|---|---|
| $C_{max}$ (μg/mL) Mean (range) | 6.133 (2.670-13.232) | 6.089 (2.908-9.514) | 6.620 (3.236-12.419) | 9.621 (3.731-19.125) |
| Standard Deviation (SD) | 2.246 | 1.954 | 2.326 | 3.860 |
| $T_{max}$ (hours) Mean | 2.286 | 3.673 | 3.273 | 1.886 |
| Median (range) | 2.33 (1.33-4.00) | 3.00 (2.00-8.00) | 2.67 (1.33-6.03) | 1.33 (0.50-8.00) |
| AUCT (μg · h/mL) | 27.48 (29.2) | 27.63 (25.6) | 28.52 (25.9) | 29.64 (27.4) |
| AUCI (μg · h/mL) | 27.86 (29.2) | 28.41 (25.6) | 29.05 (26.2) | 30.26 (27.6) |
| $T_{half}$ (hours) | 1.83 (11.7) | 1.80 (16.5) | 1.77 (13.7) | 1.79 (14.8) |

TABLE 3

Relative Bioavailability of Deferiprone Delayed-Release Tablets

| | Ratio (90% CI) | | |
|---|---|---|---|
| Parameter (units) | Deferiprone DR Fed vs. Fasted | Deferiprone DR Fed whole vs. half | Deferiprone DR vs. IR, Fed |
| $C_{max}$ (μg/mL) | 98.7 (86.6-112.4) | 89.0 (78.5-100.9) | 65.5 (57.6-74.5) |
| AUCT (μg · h/mL) | 99.0 (95.2-102.9) | 96.7 (93.2-100.4) | 92.4 (88.9-96.0) |
| AUCI (μg · h/mL) | 100.0 (96.3-103.8) | 97.5 (94.1-101.1) | 93.1 (89.7-96.7) |

TABLE 4

AUCI/Cmax

| Ratio | DR 1000 mg tablet - fasting | DR 1000 mg tablet - fed | DR 1000 mg half tablet - fed | IR 500 mg tablet - fed |
|---|---|---|---|---|
| AUCI/Cmax (hr) (range) | 4.735 (2.858-6.596) | 4.763 (3.225-8.506) | 4.423 (3.174-6.529) | 3.225 (2.073-4.497) |

Example 5: Steady State Comparative Bioavailability of Study of Deferiprone Delayed Release (DR) Tablets vs. Immediate Release (IR) Tablets at Steady State in Healthy Volunteers A 2-period crossover study was conducted to assess the comparative bioavailability of 1000 mg deferiprone DR tablets (as shown in Example 1) and deferiprone (Ferthen at specified time points post-dose over a 24-hour period on the third day (Day 3 and Day 11).

The PK comparisons between deferiprone DR and Ferriprox® IR were done at steady state (i.e., using the data for the 0-24 hour interval on the third day for each treatment).

Statistical analysis for of $AUC_{0-24hr-ss}$, $C_{max-ss}$, $C_{min-ss}$, $C_{24-ss}$, $T_{max-ss}$, are based on an ANOVA model. The two-sided 90% confidence interval of the difference between treatments were calculated for each parameter. The data of $AUC_{0-24hr-ss}$, $C_{max-ss}$, $C_{min-ss}$, and $C_{24-ss}$ were log-transformed prior to the ANOVA.

Criteria for bioequivalence in the steady state were established by the 90% confidence interval for $AUC_{0-24hr-ss}$ and $C_{max-ss}$ that needed to be within 80-125%.

Figure 4:
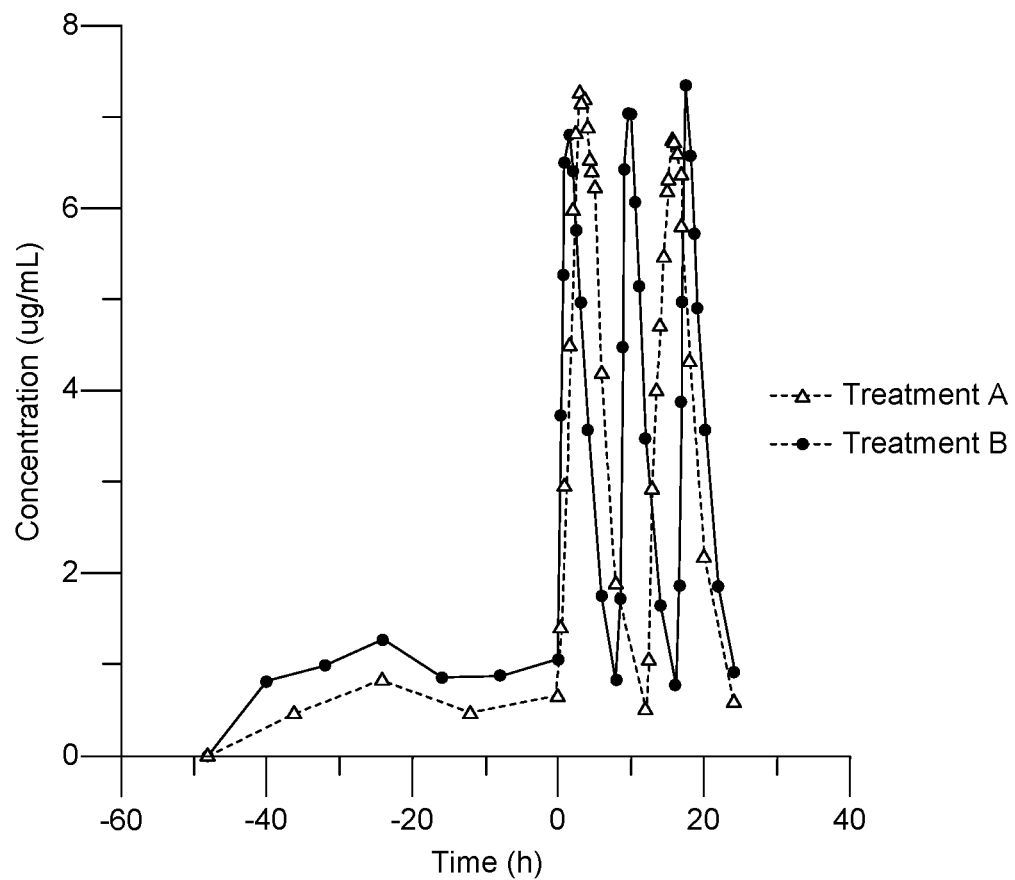
FIG. 4 shows mean serum concentration profiles of deferiprone DR and immediate release (IR) tablets.

Summaries of the study results for DR Deferiprone tablets BID and IR tablets TID in subjects at steady state are shown in Tables 5 and 6, and FIG. 4.

TABLE 5

PK Results for Deferiprone DR Tablets BID and IR Tablets TID in Subjects at Steady State

| Parameter (units) | Treatment A (Deferiprone DR) [a] (n = 35) Mean (C.V. %) | Treatment B (Deferiprone IR) [b] (n = 35) Mean (C.V. %) |
|---|---|---|
| $C_{max,\,ss}$ (µg/mL) | 9.587 (21.1) | 10.798 (27.9) |
| $T_{max,\,ss}$ (hours)[c] | 3.67 (1.50-17.00) | 9.00 (0.50-18.00) |
| $AUC_{(0-24)ss}$ (µg · h/mL) | 83.634 (22.4) | 83.364 (23.3) |

[a] One and a half 1000 mg tablets b.i.d. (every 12 hours) for a total of 3000 mg/day, for 3 consecutive days.
[b] Two 500 mg tablets t.i.d. (every 8 hours), for a total of 3000 mg/day, for 3 consecutive days.
[c] Median (range) is presented. $T_{max}$ was calculated from the 1st dose of the day.

TABLE 6

Comparison of Results for Steady State Bioequivalence of Deferiprone DR Tablets BID and IR Tablets TID

| | | 90% Confidence Limits (%) | |
|---|---|---|---|
| Parameter (units) | Ratio | Lower | Upper |
| $C_{max,\,ss}$ (µg/mL) | 88.74 | 83.00 | 94.89 |
| $AUC_{(0-24\,h)ss}$ (µg · h/mL) | 99.31 | 97.03 | 101.63 |

The results demonstrate that over a 24 hour period, the DR tablets, when given twice a day, were able to achieve the same maximum peak concentrations ($C_{max}$) as the IR tablets, when given three times a day, and that the total amount absorbed (AUC) was essentially the same for both products over a 24 hour period when the total daily dose was the same.

Example 6: Bioavailability of Deferiprone Delayed Release (DR) 600 mg Tablets vs. Oral Solution in Healthy Volunteers In this study, healthy subjects were randomized to receive the following four treatments in different orders, with a 7-day washout period between treatments:

Treatment A: Deferiprone DR, 1200 mg (two 600 mg tablets) single dose under fed conditions (n=18);

Treatment B: Deferiprone DR, 1200 mg (two 600 mg tablets) single dose under fasting conditions (n=17);

Treatment C: Deferiprone DR, 1200 mg (four half-tablets) single dose under fed conditions (n=18); and Treatment D: Oral solution (Ferriprox®), 1200 mg (100 mg/mL) single dose under fasting conditions (n=17).

Blood samples were collected pre-dose and over a 24-hour interval post-dose. PK parameters ($C_{max}$ and $T_{max}$) are shown in Table 7. The ratio of AUCI to $C_{max}$ is shown in Table 8. These results show that the $C_{max}$ for the 600 mg DR tablets is about half of the $C_{max}$ of the oral solution, and the $AUCI/C_{max}$ for the 600 mg DR tablet is about twice the ratio for the oral solution.

TABLE 7

Cmax (µg/mL) and Tmax (hr)

| Parameter (units) | Treatment A (DR 600 mg tablets - fed) | Treatment B (DR 600 mg tablets - fasted) | Treatment C (DR 600 mg half tablets - fed) | Treatment D (Oral solution - fasted) |
|---|---|---|---|---|
| $C_{max}$ (µg/mL) Mean (Range) | 8.047 (4.300-13.558) | 8.214 (5.880-13.690) | 7.429 (4.551-12.321) | 16.712 (8.613-24.059) |
| SD | 2.845 | 2.181 | 2.004 | 4.540 |
| $T_{max}$ (hr) Mean (Range; median) | 3.926 (1.333-8.000; 4.000) | 2.051 (1.333- 3.500; 2.000) | 3.494 (1.333-8.000; 3.108) | 0.522 (0.250-1.000; 0.500) |

TABLE 8

AUCI/$C_{max}$

| Ratio | Treatment A (DR 600 mg tablets - fed) | Treatment B (DR 600 mg tablets - fasted) | Treatment C (DR 600 mg half tablets - fed) | Treatment D (Oral solution - fasted) |
|---|---|---|---|---|
| AUCI/$C_{max}$ (hr) Mean (Range) | 4.758 (3.265-6.765) | 4.393 (3.511- 5.884) | 5.004 (3.567-7.589) | 2.490 (1.633-3.277) |

Example 7: Preparation of Enteric Coated Delayed Release Tablets

TABLE 9

600 mg Deferiprone Delayed Release Tablets

| Component | Function | Amount (600 mg) mg | % |
|---|---|---|---|
| Deferiprone | Active | 600 | 87.7 |
| Hypromellose Acetate Succinate(NF) AS-LF | Release controlling polymer | 29.5 | 4.31 |
| Magnesium oxide | pH adjusting agent | 24.5 | 3.58 |
| Colloidal Silicon Dioxide (part 1) | Glidant | 1 | 0.1462 |
| Subtotal Post Compaction | | 655 | 95.7 |
| Magnesium stearate | Lubricant | 4 | 0.585 |
| Colloidal Silicon Dioxide (part 2) | Glidant | 1 | 0.1462 |
| Total | | 660 | 96.5 |
| Coating | | | |
| Triethyl Citrate NF | Plasticizer | 1.032 | 0.1509 |
| Sucrose NF (extra fine) | Coating agent | 3.09 | 0.452 |
| Talc USP 500 mesh | Anti-tacking agent | 2.09 | 0.306 |
| *Methacrylic Acid Copolymer Dispersion NF | Release controlling polymer | 30.96 | 4.53 |
| Titanium Dioxide USP | Opacifying agent | 8.5 | 1.243 |
| **Purified Water | | 154.3 | 22.6 |
| TOTAL COATED TABLET | | 684 | 100 |

*Contains 30% solids.
**Evaporates during the coating process.

To prepare the tablet core, deferiprone, hypromellose acetate succinate(NF) AS-LF, magnesium oxide light USP/EP, and colloidal silicon dioxide (part 1) were mixed together, and the mixture was compacted and milled into granules. Magnesium stearate and colloidal silicon dioxide (part 2) were added to and blended with the granules. The resulting mixture was compressed into core tablets. The tablets were then coated.

In addition to the various embodiments described herein, the present disclosure includes the following embodiments numbered E1 through E132. This list of embodiments is presented as an exemplary list and the application is not limited to these embodiments.

E1. A delayed release tablet comprising deferiprone for oral administration to a human subject, wherein twice daily administration of the delayed release tablet is bioequivalent in the steady state to the same daily dose of an immediate release tablet comprising deferiprone administered three times daily.

E2. The tablet according to E1, wherein the tablet is a whole tablet that is scored to facilitate breakage into half tablets.

E3. The tablet according to E2, wherein the half tablets are bioequivalent to the whole tablet in either the fasted state or the fed state.

E4. The tablet according to E3, wherein half tablets are bioequivalent to the whole tablet in both the fasted state and the fed state.

E5. The tablet according to any one of E1 to E4, wherein the tablet consists of: (a) a core comprising deferiprone in a therapeutically effective amount and (b) an enteric coating.

E6. The tablet according to E5, wherein the core further comprises an enteric polymer.

E7. The tablet according to E6, wherein the enteric polymer in the core is selected from the group consisting of hydroxypropyl methylcellulose (HPMC) acetate succinate, HPMC phthalate, polyvinyl acetate phthalate, methacrylic acid copolymers, a derivative thereof, and a combination thereof.

E8. The tablet according to E7, wherein the enteric polymer is present in an amount of about 1% to about 20% by weight of the core.

E9. The tablet according to any one of E1 to E8, wherein a single dose of the tablet provides a mean $AUC_\infty/C_{max}$ ratio between 3.5 hours and 6.0 hours in fasted state when the tablet is administered to human subjects.

E10. The tablet according to any one of E1 to E8, wherein a single dose of the tablet provides a mean $AUC_\infty/C_{max}$ ratio between 3.5 hours and 6.0 hours in fed state when the tablet is administered to human subjects.

E11. The tablet according to E9 or E10, wherein the tablet comprises 1000 mg deferiprone.

E12. The tablet according to E9 or E10, wherein the tablet comprises 600 mg deferiprone.

E13. The tablet according to E11, wherein the mean $C_{max}$ is between 2.670 and 13.232 µg/mL when the tablet is administered to human subjects.

E14. The tablet according to E11, wherein the median $T_{max}$ is between 1.33 and 4.00 hours when the tablet is administered to human subjects.

E15. The tablet according to E11, wherein the median $T_{max}$ is between 2.00 and 8.00 hours when the tablet is administered to human subjects.

E16. The tablet according to E11, wherein the median $T_{max}$ is between 1.33 and 6.03 hours when the tablet is administered to human subjects.

E17. The tablet according to E11, wherein the ratio of $AUCI/C_{max}$ is between 2.858 to 6.596 hours when the tablet is administered to human subjects.

E18. The tablet according to E11, wherein the ratio of $AUCI/C_{max}$ is between 3.225 to 8.506 hours when the tablet is administered to human subjects.

E19. A tablet for oral administration of an active pharmaceutical ingredient to a human subject, wherein the tablet comprises: (a) a core comprising the active pharmaceutical ingredient in a therapeutically effective amount and an enteric polymer, and (b) an enteric coating, wherein the tablet is scored such that it can be administered as a whole tablet or a half tablet and wherein if the tablet is administered as one or more half tablets, the half tablets are bioequivalent to the whole tablets in either the fasted state or the fed state.

E20. The tablet of E19, wherein the enteric polymer in the core is selected from the group consisting of hydroxypropyl methylcellulose acetate succinate (HPMCAS), HPMC phthalate, polyvinyl acetate phthalate, methacrylic acid copolymers, a derivative thereof, and a combination thereof.

E21. The tablet of E20, wherein the enteric polymer is present in an amount of about 1% to about 20% by weight of the core.

E22. The tablet according to any one of E19 to E21, wherein the active pharmaceutical ingredient is deferiprone.

E23. The tablet according to any one of E19 to E22, wherein twice daily administration of the tablet is bioequivalent in the steady state to the same daily dose of the immediate release (Ferriprox®) tablet comprising deferiprone administered three times daily.

E24. The tablet according to any one of E19 to E23, wherein a single dose of the tablet provides a mean $AUC_\infty/C_{max}$ ratio between 3.5 hours and 6.0 hours in fasted state when the tablet is administered to human subjects.

E25. The tablet according to any one of E19 to E23, wherein a single dose of the tablet provides a mean $AUC_\infty/C_{max}$ ratio between 3.5 hours and 6.0 hours in fed state when the tablet is administered to human subjects.

E26. The tablet according to E24 or E25, wherein the tablet comprises 1000 mg deferiprone.

E27. The tablet according to E24 or E25, wherein the tablet comprises 600 mg deferiprone.

E28. The tablet according to E26, wherein the mean $C_{max}$ is between 2.670 and 13.232 μg/mL when the tablet is administered to human subjects.

E29. The tablet according to E26, wherein the median $T_{max}$ is between 1.33 and 4.00 hours when the tablet is administered to human subjects.

E30. The tablet according to E26, wherein the median $T_{max}$ is between 2.00 and 8.00 hours when the tablet is administered to human subjects.

E31. The tablet according to E26, wherein the median $T_{max}$ is between 1.33 and 6.03 hours when the tablet is administered to human subjects.

E32. The tablet according to E26, wherein the ratio of $AUCI/C_{max}$ is between 2.858 to 6.596 hours when the tablet is administered to human subjects.

E33. The tablet according to E26, wherein the ratio of $AUCI/C_{max}$ is between 3.225 to 8.506 hours when the tablet is administered to human subjects.

E34. A tablet for oral administration of an active pharmaceutical ingredient comprising: (a) a core comprising the active pharmaceutical ingredient in a therapeutically effective amount and an enteric polymer, and (b) an enteric coating, the tablet being a whole tablet which is scored to facilitate breakage of the tablet into half tablets, wherein both the whole and the half tablets display a delayed release dissolution profile.

E35. The tablet according to E34, wherein the half tablets are bioequivalent to the whole tablets in either the fasted state or the fed state.

E36. The tablet according to E35, wherein the enteric polymer in the core is selected from the group consisting of hydroxypropyl methylcellulose acetate succinate (HPMCAS), HPMC phthalate, polyvinyl acetate phthalate, methacrylic acid copolymers, a derivative thereof, and a combination thereof.

E37. The tablet according to E36, wherein the enteric polymer is present in an amount of about 1% to about 20% by weight of the core.

E38. The tablet according to any one of E34 to E37, wherein the active pharmaceutical ingredient is deferiprone.

E39. The tablet according to any one of E34 to E38 wherein both the whole and the half tablets exhibit dissolution below 20% at 60 minutes in 0.1 N HCl.

E40. The tablet according to any one of E34 to E39, wherein a single dose of the tablet provides a mean $AUC_\infty/C_{max}$ ratio between 3.5 hours and 6.0 hours in fasted state when the tablet is administered to human subjects.

E41. The tablet according to any one of E34 to E39, wherein a single dose of the tablet provides a mean $AUC_\infty/C_{max}$ ratio between 3.5 hours and 6.0 hours in fed state when the tablet is administered to human subjects.

E42. The tablet according to E40 or E41, wherein the tablet comprises 1000 mg deferiprone.

E43 The tablet according to E40 or E41, wherein the tablet comprises 600 mg deferiprone.

E44. The tablet according to E42, wherein the mean $C_{max}$ is between 2.670 and 13.232 μg/mL when the tablet is administered to human subjects.

E45. The tablet according to E42, wherein the median $T_{max}$ is between 1.33 and 4.00 hours when the tablet is administered to human subjects.

E46. The tablet according to E42, wherein the median $T_{max}$ is between 2.00 and 8.00 hours when the tablet is administered to human subjects.

E47. The tablet according to E42, wherein the median $T_{max}$ is between 1.33 and 6.03 hours when the tablet is administered to human subjects.

E48. The tablet according to E42, wherein the ratio of $AUCI/C_{max}$ is between 2.858 to 6.596 hours when the tablet is administered to human subjects.

E49. The tablet according to E42, wherein the ratio of $AUCI/C_{max}$ is between 3.225 to 8.506 hours when the tablet is administered to human subjects.

E50. A tablet for oral administration comprising: (a) a core comprising deferiprone in a therapeutically effective amount and an enteric polymer; and (b) an enteric coating comprising an enteric polymer, wherein the tablet is suitable for twice daily dosing.

E51. The tablet of E50 which is scored to facilitate breakage of the tablet into half tablets.

E52. The tablet of E51 which can be administered as one or more whole tablets, one or more half tablets, or a combination thereof.

E53. The tablet according to any one of E50 to E52, wherein the enteric polymer in the core is selected from the group consisting of hydroxypropyl methylcellulose acetate succinate (HPMCAS), HPMC phthalate, polyvinyl acetate phthalate, methacrylic acid copolymers, a derivative thereof, and a combination thereof.

E54. The tablet according to E53, wherein the enteric polymer is present in an amount of about 1% to about 20% by weight of the core.

E55. The tablet according to any one of E50 to E54, wherein the enteric polymer in the enteric coating is selected from the group consisting of hydroxypropyl methylcellulose acetate succinate (HPMCAS), HPMC phthalate, polyvinyl acetate phthalate, methacrylic acid copolymers, a derivative thereof, and a combination thereof.

E56. The tablet according to any one of E50 to E55, wherein the core further comprises a basic excipient and a glidant.

E57. The tablet according to E56, wherein the basic excipient is selected from the group consisting meglumine, metal oxides, metal hydroxides, basic salts of weak acids, and a combination thereof.

E58. The tablet according to E56 or E57, wherein the glidant is colloidal silicon dioxide.

E59. The tablet according to any one of E56 to E58 further comprising a lubricant.

E60. The tablet according to E59, wherein the lubricant is selected from the group consisting of magnesium stearate, calcium stearate, stearic acid, sodium stearyl fumarate, talc, and a combination thereof.

E61. The tablet according to any one of E54 to E60, wherein the enteric coating further comprises a plasticizer and an anti-tacking agent.

E62. The tablet according to E61, wherein the plasticizer is selected from the group consisting of a citrate ester, diethyl phthalate, polyethylene glycol, glycerol, acetylated glycerides, acetylated citrate esters, dibutyl sebecate, castor oil, and a combination thereof.

E63. The tablet according to E61 or E62, wherein the tablet further comprises a diluent selected from the group consisting of sucrose, lactose, fructose, mannitol, and a combination thereof.

E64. The tablet according to E61 or E62, wherein the anti-tacking agent is talc.

E65. The tablet according to any one of E50 to E64, wherein a single dose of the tablet provides a mean $AUC_\infty/C_{max}$ ratio between 3.5 hours and 6.0 hours in fasted state when the tablet is administered to human subject.

E66. The tablet according to any one of E50 to E64, wherein a single dose of the tablet provides a mean $AUC_\infty/C_{max}$ ratio between 3.5 hours and 6.0 hours in fed state when the tablet is administered to human subjects.

E67. The tablet according to E65 or E66, wherein the tablet comprises 1000 mg deferiprone.

E68. The tablet according to E65 or 66, wherein the tablet comprises 600 mg deferiprone.

E69. The tablet according to E67, wherein the mean $C_{max}$ is between 2.670 and 13.232 µg/mL when the tablet is administered to human subjects.

E70. The tablet according to E67, wherein the median $T_{max}$ is between 1.33 and 4.00 hours when the tablet is administered to human subjects.

E71. The tablet according to E67, wherein the median $T_{max}$ is between 2.00 and 8.00 hours when the tablet is administered to human subjects.

E72. The tablet according to E67, wherein the median $T_{max}$ is between 1.33 and 6.03 hours when the tablet is administered to human subjects.

E73. The tablet according to E67, wherein the ratio of $AUCI/C_{max}$ is between 2.858 to 6.596 hours when the tablet is administered to human subjects.

E74. The tablet according to E67, wherein the ratio of $AUCI/C_{max}$ is between 3.225 to 8.506 hours. when the tablet is administered to human subjects.

E75. A tablet comprising deferiprone for twice daily oral administration, wherein a single dose administration of the tablet provides a mean $AUC_\infty/C_{max}$ ratio between 3.5 hours and 6.0 hours in both fasted and fed state when the tablet is administered as a whole tablet and when administered to human subjects as a half tablet.

E76. The tablet according to E75, wherein the mean $AUC_\infty/C_{max}$ ratio is about 4.0 hours to about 5.5 hours.

E77. The tablet according to E75 or E76, where the active pharmaceutical ingredient or the deferiprone is in an amount of about 100 mg to about 1500 mg per tablet.

E78. The tablet according to any one of E75 to E77, wherein the total daily dose of the active pharmaceutical ingredient or the deferiprone is about 100 mg/day, about 200 mg/day, about 300 mg/day, about 400 mg/day, about 500 mg/day, about 600 mg/day, about 700 mg/day, about 800 mg/day, about 900 mg/day, about 1000 mg/day, about 1200 mg/day, about 1500 mg/day, about 1800 mg/day, about 2000 mg/day, about 2100 mg/day, about 2400 mg/day, about 2500 mg/day, about 2700 mg/day, about 3000 mg/day, about 3300 mg/day, about 3500 mg/day, about 4000 mg/day, about 4500 mg/day, about 5000 mg/day, about 5500 mg/day, about 6000 mg/day, about 6500 mg/day, about 7000 mg/day, about 7500 mg/day, about 8000 mg/day, about 8500 mg/day, about 9000 mg/day, about 9500 mg/day, or about 10,000 mg/day.

E79. The tablet according to any of E74 to E78, where the active pharmaceutical ingredient or the deferiprone is in an amount of about 100 mg, about 200 mg, about 250 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, or about 1500 mg per tablet.

E80. The tablet according to E79 which comprises a core comprising about 1000 mg or about 600 mg of deferiprone, about 20 mg to about 80 mg of an enteric polymer, and about 5 mg to about 100 mg of a basic excipient.

E81. The tablet according to E80, further comprising a lubricant in an amount of about 7 mg to about 20 mg.

E82. The tablet according to E80 or E81 which comprises an enteric coating comprising about 7 mg to about 20 mg of an enteric polymer, and about 0.5 mg to about 5 mg of a plasticizer.

E83. The tablet according to E79 which comprises a core comprising about 600 mg deferiprone, about 20 mg to about 80 mg of an enteric polymer, and about 5 mg to about 100 mg of a basic excipient.

E84. The tablet according to E83, further comprising a lubricant in an amount of about 2 mg to about 10 mg.

E85. The tablet according to E83 or E84 which comprises an enteric coating comprises about 5 mg to about 20 mg of an enteric polymer, and about 0.5 mg to about 5 mg of a plasticizer.

E86. The tablet according to any one of E75 to E85, wherein the tablet comprises 1000 mg deferiprone.

E87. The tablet according to any one of E75 to E85, wherein the tablet comprises 600 mg deferiprone.

E88. The tablet according to E86, wherein the mean $C_{max}$ is between 2.670 and 13.232 µg/mL when the tablet is administered to human subjects.

E89. The tablet according to E86, wherein the median $T_{max}$ is between 1.33 and 4.00 hours when the tablet is administered to human subjects.

E90. The tablet according to E86, wherein the median $T_{max}$ is between 2.00 and 8.00 hours when the tablet is administered to human subjects.

E91. The tablet according to E86, wherein the median $T_{max}$ is between 1.33 and 6.03 hours when the tablet is administered to human subjects.

E92. The tablet according to E86, wherein the ratio of $AUCI/C_{max}$ is between 2.858 to 6.596 hours when the tablet is administered to human subjects.

E93. The tablet according to E86, wherein the ratio of $AUCI/C_{max}$ is between 3.225 to 8.506 hours when the tablet is administered to human subjects.

E94. The tablet according to any one of E1 to E93 which is scored to facilitate breakage of the tablet into half tablets and can be administered to a human subject as one or more whole tablets, one or more half tablets, or any combination thereof.

E95. The tablet according to any one of E1 to E94, wherein the tablet releases less than about 80% of the deferiprone within 60 minutes when measured by USP Apparatus Type II Paddle Method at 75 rpm in 900 mL water at 37±0.5° C.

E96. The tablet according to E95, wherein approximately 100% of the deferiprone is released within about 90 minutes when measured by USP Apparatus Type II Paddle Method at 75 rpm in 900 mL at pH 6.8 or 4.5.

E97. The tablet according to E96, wherein approximately 50% of the deferiprone is released within about 30 minutes when measured by USP Apparatus Type II Paddle Method at 75 rpm in 900 mL at pH 6.8 or 4.5.

E98. A method for treating a subject with iron overload, comprising orally administering to the subject in need thereof the tablet of any one of E1 to E97.

E99. The method according to E98, wherein the subject suffers from thalassemia or myelodysplasia.

E100. The method according to E98, wherein the subject suffers from transfusional iron overload and whose prior chelation therapy is inadequate.

E101. The method according to E98, wherein the subject suffers from transfusional iron overload and has a cardiac MM T2* of 20 ms or less.

E102. A method for treating a subject with a neurodegenerative disease, comprising orally administering to the subject in need thereof the tablet of any one of E1 to E97.

E103. The method of E102, wherein the subject suffers from Parkinson's disease, amyotrophic lateral sclerosis (ALS), Huntington's disease, Friedreich's Ataxia, Pantothenate Kinase Associated Neurodegeneration (PKAN), or neurodegeneration with brain iron accumulation (NBIA).

E104. The method according to any one of E98 to E103, comprising a regimen of once daily or twice daily dosing (BID).

E105. The method according to any one of E98 to E104, wherein the tablet is administered to the subject as one or more whole tablets, one or more half tablets, or a combination thereof.

E106. The method according to any one of E98 to E105, wherein the tablet is administered to the subject in a fasted state or a fed state.

E107. The method according to any one of E98 to E106, wherein the deferiprone is in an amount of about 100 mg to about 800 mg per tablet.

E108. The method according to any one of E98 to E107, wherein the deferiprone is in an amount of about 400 mg per tablet.

E109. The method according to any one of E98 to E108, wherein the total daily dose of deferiprone is about 200 mg/day to about 2400 mg/day.

E110. The method according to any one of E98 to E109, wherein the total daily dose of deferiprone is about 400 mg/day to about 1200 mg/day.

E111. The method according to any one of E98 to E110, wherein the tablet is administered once or twice a day.

E112. The method according to any one of E98 to E111, wherein one, two or three tablets are administered once or twice a day.

E113. The method according to any one of E98 to E112, wherein one, two or three tablets are administered once, twice, or three times a day.

E113. The method according to any one of E103 to E112, wherein the subject suffers from amyotrophic lateral sclerosis (ALS).

E114. The method according to any one of E103 to E113, wherein the treatment reduces or slows progression of a disability associated with ALS in the subject.

E115. The method according to E113 or E114, further comprising administering riluzole to the subject.

E116. A method for treating a human subject with iron overload, comprising orally administering to the subject in need thereof 3000 mg/day deferiprone, wherein the subject is administered the deferiprone two times per day.

E117. The method according to E116, wherein the subject suffers from thalassemia or myelodysplasia.

E118. The method according to E116 or E117, wherein the 3000 mg/day deferiprone is administered at a dose of 1500 mg two times a day.

E119. The method according to any one of E116 to E118, wherein the subject exhibits a $C_{max}$ of 48.5-10.5 µg/mL at steady state.

E120. The method according to any one of E116 to E119, wherein the subject exhibits an $AUC_{(0-24)}$ of 75-95 µg·h/mL at steady state.

E121. The method according to any one of E98 to E120, wherein the subject is administered a tablet of any one of E1 to E97.

E122. A method for treating a human subject with iron overload, comprising orally administering to the subject in need thereof 1200 mg/day deferiprone, wherein the subject is administered the deferiprone two times per day.

E123. The method according to E122, wherein the subject suffers from a neurogenic disease.

E124. The method according to E122 or E123, wherein the 1200 mg/day deferiprone is administered at a dose of 600 mg two times a day.

E125. The method according to any one of E122 or E124, wherein the 1200 mg/day deferiprone is administered at a dose of 1200 mg one time per day.

E126. The method according to any one of E122 to E125, wherein the subject exhibits a $C_{max}$ of 4.00 to 13.558 µg/mL after administration of 600 mg deferiprone in the fed state.

E127. The method according to any one of E122 to E126, wherein the subject exhibits a $C_{max}$ of 5.880 to 13.690 µg/mL after 600 mg deferiprone in the fasted state.

E128. The method according to any one of E122 to E127, wherein the subject exhibits a $T_{max}$ of 1.333 to 8.000 hours after administration of 1200 mg deferiprone.

E129. The method according to any one of E122 to E128, wherein the subject exhibits a $AUCl/C_{max}$ of 3.265 to 6.765 hr after administration of 1200 mg deferiprone.

E130. The method according to any one of E122 to E129, wherein the subject suffers from transfusional iron overload and whose prior chelation therapy is inadequate.

E131. The method according to any one of E122 to E129, wherein the subject suffers from transfusional iron overload and has a cardiac MM T2* of 20 ms of less.

E132. The method according to any one of E122 to E131, wherein the subject is administered a tablet of any one of E1 to E97.

E133. A tablet for oral administration comprising: (a) a core comprising 1000 mg or 600 mg of deferiprone, an enteric polymer, a pH adjusting agent, a glidant, and a lubricant; and (b) an enteric coating comprising a plasticizer, a diluent, an anti-tacking agent, and an enteric polymer, wherein the tablet is suitable for twice daily dosing, the tablet being a whole tablet which is scored to facilitate breakage of the tablet into half tablets.

What is claimed is:

1. A method for reducing gastric distress or the risk of gastric distress in a patient in need of deferiprone treatment, comprising orally administering to the patient a tablet comprising (a) a core comprising about 1000 mg deferiprone and an enteric polymer; and (b) an enteric coating comprising an enteric polymer, wherein the tablet is suitable for twice daily dosing.

2. The method of claim 1, wherein the enteric coating is about 0.5% to about 20% of the total weight of the tablet.

3. The method of claim 2, wherein the enteric coating is about 1% to about 10% of the total weight of the tablet.

4. The method of claim 2, wherein the enteric coating is about 0.5% to about 5% of the total weight of the tablet.

5. The method of claim 1, wherein the enteric polymer in the coating is about 0.5% to about 4% by weight of the tablet.

6. The method of claim 5, wherein the enteric polymer in the coating is about 1% to about 2% by weight of the tablet.

7. The method of claim 5, wherein the enteric polymer in the coating is about 0.5% to about 1% by weight of the tablet.

8. The method of claim 1, wherein the enteric coating comprises about 5 mg to about 30 mg of an enteric polymer.

9. The method of claim 8, wherein the enteric coating comprises about 7 mg to about 20 mg of an enteric polymer.

10. The method of claim 8, wherein the enteric coating comprises about 8 mg to about 15 mg of an enteric polymer.

11. The method of claim 1, wherein the deferiprone is about 75% to about 95% of the total core weight.

12. The method of claim 11, wherein the deferiprone is about 80% to about 95% of the total core weight.

13. The method of claim 11, wherein the deferiprone is about 85% to about 95% of the total core weight.

14. The method of claim 1, wherein the core further comprises a basic excipient.

15. The method of claim 14, wherein the basic excipient is about 1% to about 10% of the total weight of the core.

16. The method of claim 15, wherein the basic excipient is about 1% to about 5% of the total weight of the core.

17. The method of claim 1, wherein the core further comprises a lubricant.

18. The method of claim 17, wherein the core comprises about 2 mg to about 25 mg of the lubricant.

19. The method of claim 18, wherein the core comprises about 2 mg to about 10 mg of the lubricant.

20. The method of claim 18, wherein the core comprises about 10 mg to about 20 mg of the lubricant.

21. The method of claim 1, wherein the enteric polymer is about 1.0% to about 5.0% of the total weight of the core.

22. The method of claim 1, wherein the enteric polymer is about 2.0% to about 4.0% of the total weight of the core.

23. The method of claim 1, wherein the enteric polymer is about 2.5% of the total weight of the core.

24. The method of claim 1, wherein the gastric distress is reduced as compared to orally administering to the patient an immediate release deferiprone tablet.

* * * * *